US012582649B2

(12) United States Patent
Hu

(10) Patent No.: US 12,582,649 B2

(45) Date of Patent: Mar. 24, 2026

(54) COMPOSITIONS AND METHODS FOR HAIR FOLLICLE REGENERATION

(71) Applicant: Washington University, St. Louis, MO (US)

(72) Inventor: Hongzhen Hu, St. Louis, MO (US)

(73) Assignee: Washington University, St. Louis, MO (US)

( * ) Notice: Subject to any disclaimer, the term of this patent is extended or adjusted under 35 U.S.C. 154(b) by 594 days.

(21) Appl. No.: 18/009,050

(22) PCT Filed: Jun. 3, 2021

(86) PCT No.: PCT/US2021/035659
§ 371 (c)(1),
(2) Date: Dec. 8, 2022

(87) PCT Pub. No.: WO2021/252261
PCT Pub. Date: Dec. 16, 2021

(65) Prior Publication Data

US 2023/0277528 A1 Sep. 7, 2023

Related U.S. Application Data

(60) Provisional application No. 63/036,267, filed on Jun. 8, 2020.

(51) Int. Cl.

| | |
|---|---|
| ***A61K 31/4965*** | (2006.01) |
| ***A61K 9/00*** | (2006.01) |
| ***A61K 31/352*** | (2006.01) |
| ***A61P 17/14*** | (2006.01) |

(52) U.S. Cl.
CPC ........ *A61K 31/4965* (2013.01); *A61K 9/0014* (2013.01); *A61K 31/352* (2013.01); *A61P 17/14* (2018.01)

(58) Field of Classification Search
CPC .. A61K 31/4965; A61K 9/0014; A61K 8/494; A61K 8/4973; A61K 8/498; A61K 8/4986; A61K 31/352; A61K 31/558; A61K 31/6615; A61K 2300/00; A61P 17/14; A61Q 7/00
USPC ..................................................... 514/252.13
See application file for complete search history.

(56) References Cited

U.S. PATENT DOCUMENTS 9,737,469 B2 8/2017 Christiano et al.

OTHER PUBLICATIONS

Alexander et al. (2019) The Concise Guide to Pharmacology 2019/20: Introduction and Other Protein Targets. Br J Pharmacol 176 Suppl 1: S1-S20.
Ali et al. (2017) Regulatory T Cells in Skin Facilitate Epithelial Stem Cell Differentiation. Cell 169: 1119-1129 e1111.
Amberg et al. (2016) Effects of Imiquimod on Hair Follicle Stem Cells and Hair Cycle Progression. J Invest Dermatol 136: 2140-2149.
Borbiro et al. (2011) Activation of transient receptor potential vanilloid-3 inhibits human hair growth. J Invest Dermatol 131: 1605-1614.

(Continued)

*Primary Examiner* — Taylor V Oh

(57) ABSTRACT

Among the various aspects of the present disclosure is the provision of compositions and methods for treating hair regeneration disorders or conditions such as hair loss or thinning. An aspect of the present disclosure provides for a method of treating hair loss, promoting hair growth, or treating hair loss, such as alopecia or telogen effluvium, comprising administering a TRPV4 activating agent to a subject.

22 Claims, 12 Drawing Sheets

Specification includes a Sequence Listing.

(56) References Cited

OTHER PUBLICATIONS

Caterina et al. (2016) TRP Channels in Skin Biology and Pathophysiology. Pharmaceuticals (Basel) 9.
Chen et al. (2015) Organ-level quorum sensing directs regeneration in hair stem cell populations. Cell 161: 277-290.
Chen et al. (2016) Transient Receptor Potential Vanilloid 4 Ion Channel Functions as a Pruriceptor in Epidermal Keratinocytes to Evoke Histaminergic Itch. J Biol Chem 291:10252-10262.
Cheng et al. (2010) TRP channel regulates EGFR signaling in hair morphogenesis and skin barrier formation. Cell 141: 331-343.
Denda et al. (2007) Effects of skin surface temperature on epidermal permeability barrier homeostasis. J Invest Dermatol 127: 654-659.
Enshell-Seijffers et al. (2010) beta-catenin activity in the dermal papilla regulates morphogenesis and regeneration of hair. Dev Cell 18: 633-642.
Gazzerro et al. (1998) Bone morphogenetic proteins induce the expression of noggin, which limits their activity in cultured rat osteoblasts. J Clin Invest 102: 2106-2114.
Greco et al. (2009) A two-step mechanism for stem cell activation during hair regeneration. Cell Stem Cell 4: 155-169.
Harding et al. (2018) The IUPHAR/BPS Guide to Pharmacology in 2018: updates and expansion to encompass the new guide to Immunopharmacology. Nucleic Acids Res 46: D1091-D1106.
Hsu et al. (2011) Dynamics between stem cells, niche, and progeny in the hair follicle. Cell 144:92-105.
Imura et al. (2007) Influence of TRPV3 mutation on hair growth cycle in mice. Biochem Biophys Res Commun 363: 479-483.
International Search Report for PCT/US21/35659 dated Oct. 14, 2021, 2 pages.
Ito et al. (1999) Noggin and bone morphogenetic protein-4 coordinately regulate the progression of chondrogenic differentiation in mouse clonal EC cells, ATDC5. Biochem Biophys Res Commun 260: 240-244.
Kandyba et al. (2013) Competitive balance of intrabulge BMP/Wnt signaling reveals a robust gene network ruling stem cell homeostasis and cyclic activation. Proc Natl Acad Sci U S A 110: 1351-1356.
Kida et al. (2012) Importance of transient receptor potential vanilloid 4 (TRPV4) in epidermal barrier function in human skin keratinocytes. Pflugers Arch 463: 715-725.
Li et al. (2012) VEGF induces proliferation of human hair follicle dermal papilla cells through VEGFR-2-mediated activation of ERK. Exp Cell Res 318: 1633-1640.
Lin et al. (2012) Exome sequencing reveals mutations in TRPV3 as a cause of Olmsted syndrome. Am J Hum Genet 90: 558-564.
Luo et al. (2014) Thermally activated TRPV3 channels. Curr Top Membr 74: 325-364.
Luo et al. (2018) Transient receptor potential vanilloid 4-expressing macrophages and keratinocytes contribute differentially to allergic and nonallergic chronic itch. J Allergy Clin Immunol 141: 608-619 e7.
Mamenko et al. (2015) Deciphering physiological role of the mechanosensitive TRPV4 channel in the distal nephron. Am J Physiol Renal Physiol 308: F275-F286.
Mcgrath et al. (2015) Implementing guidelines on reporting research using animals (Arrive etc.): new requirements for publication in BJP. Br J Pharmacol 172: 3189-3193.
Moore et al. (2013) UVB radiation generates sunburn pain and affects skin by activating epidermal TRPV4 ion channels and triggering endothelin-1 signaling. Proc Natl Acad Sci U S A 110: E3225-3234.
Muller-Rover et al. (2001) A comprehensive guide for the accurate classification of murine hair follicles in distinct hair cycle stages. J Invest Dermatol 117: 3-15.
Nilius et al. (2014) Transient receptor potential channels as drug targets: from the science of basic research to the art of medicine. Pharmacol Rev 66: 676-814.
Oshima et al. (2001) Morphogenesis and renewal of hair follicles from adult multipotent stem cells. Cell 104: 233-245.
Paus et al. (1999) The biology of hair follicles. N Engl J Med 341: 491-497.
Plikus et al. (2008) Cyclic dermal BMP signalling regulates stem cell activation during hair regeneration. Nature 451: 340-344.
Reinhold et al. (2004) FGF18 represses noggin expression 490 and is induced by calcineurin. J Biol Chem 279: 38209-38219.
Schmidt-Ullrich et al. (2005) Molecular principles of hair follicle induction and morphogenesis. Bioessays 27:247-261.
Sharma et al. (2017) TRPV4 ion channel is a novel regulator of dermal myofibroblast differentiation. Am J Physiol Cell Physiol 312: C562-C572.
Sokabe et al. (2010a) The TRPV4 cation channel: A molecule linking skin temperature and barrier function. Commun Integr Biol 3: 619-621.
Sokabe et al. (2010b) The TRPV4 channel contributes to intercellular junction formation in keratinocytes. J Biol Chem 285: 18749-18758.
Song et al. (2010) Identification of a key residue mediating bone morphogenetic protein (BMP)-6 resistance to noggin inhibition allows for engineered BMPs with superior agonist activity. J Biol Chem 285: 12169-12180.
Suzuki et al. (2003) Impaired pressure sensation in mice lacking TRPV4. J Biol Chem 278(25):22664-22668.
Szabo et al. (2019) TRPV4 Is Expressed in Human Hair Follicles and Inhibits Hair Growth In Vitro. J Invest Dermatol 139: 1385-1388.
Thorneloe et al. (2008) N-((1S)-1-{[4-((2S)-2-{[(2,4-dichlorophenyl)sulfonyl]amino}-3-hydroxypropanoyl)-1-piperazinyl]carbonyl}-3-methylbutyl)-1-benzothiophene-2-carboxamide (GSK1016790A), a novel and potent transient receptor potential vanilloid 4 channel agonist induces urinary bladder contraction and hyperactivity: Part I. J Pharmacol Exp Ther 326: 432-442.
Thorneloe et al. (2012) An orally active TRPV4 channel blocker prevents and resolves pulmonary edema induced by heart failure. Sci Transl Med 4: 159ra148.
Toth et al. (2014) TRP channels in the skin. Br J Pharmacol 171: 2568-2581.
Voets (2014) TRP Channels and Thermosensation. Handb Exp Pharmacol 223: 729-741.
Voets et al. (2002) Molecular determinants of permeation through the cation channel TRPV4. Journal of Biological Chemistry 277: 33704-33710.
Wang et al. (2017) Macrophages induce AKT/beta-catenin dependent Lgr5(+) stem cell activation and hair follicle regeneration through TNF. Nat Commun 8: 14091.
Written Opinion for PCT/US21/35659 dated Oct. 14, 2021, 5 pages.
Xiao et al. (2008) The TRPV3 mutation associated with the hairless phenotype in rodents is constitutively active. Cell Calcium 43: 334-343.
Yang et al. (2020) Transient stimulation of TRPV4-expressing keratinocytes promotes hair follicle growth regeneration in mice. Br J Pharmacol. 177:4181-4192.
Ye et al. (2012) TRPV4 is a regulator of adipose oxidative metabolism, inflammation, and energy homeostasis. Cell 151: 96-110.

Back tape stripping plus

Gsk101 100μM, 1times Vehicle

Wild type

Back tape stripping only

Wild type

Trpv4 ko

COMPOSITIONS AND METHODS FOR HAIR FOLLICLE REGENERATION

CROSS-REFERENCE TO RELATED APPLICATIONS

This application claims priority from U.S. Provisional Application Ser. No. 63/036,267 filed on 8 Jun. 2020, which is incorporated herein by reference in its entirety.

STATEMENT REGARDING FEDERALLY SPONSORED RESEARCH OR DEVELOPMENT

This application is a national stage entry of PCT International Application No. PCT/US2021/035659 filed on 3 Jun. 2021, which claims the benefit of priority to U.S. Provisional Application Ser. No. 63/036,267 filed on 8 Jun. 2020, which are incorporated herein by reference in their entireties.

MATERIAL INCORPORATED-BY-REFERENCE

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The present disclosure generally relates to hair loss treatment or hair follicle regeneration.

SUMMARY

Among the various aspects of the present disclosure is the provision of compositions and methods for regenerating hair follicles or treating hair loss or thinning.

An aspect of the present disclosure provides for a method of treating or preventing hair loss or promoting hair growth comprising administering a therapeutically effective amount of a TRPV4 activating agent to a subject in need thereof. Another aspect of the present disclosure provides for a method of inducing hair follicle regeneration comprising administering a TRPV4 activating agent to a subject in need thereof. Yet another aspect of the present disclosure provides for a method of inducing telogen-anagen transition in a hair follicle cell comprising administering a therapeutically effective amount of a TRPV4 activating agent to a subject in need thereof. Yet another aspect of the present disclosure provides for a method of increasing expression or upregulating an anagen-activating factor and decreasing expression of or downregulating an anagen-inhibiting factor in a cell comprising administering a TRPV4 activating agent to the cell. In some embodiments, the hair follicle cell is selected from a quiescent stem cell or TRPV4-expressing cell. In some embodiments, the TRPV4-expressing cell is a fibroblast or adipocyte. In some embodiments, the subject has alopecia. In some embodiments, the subject has thinning hair. In some embodiments, the subject has telogen effluvium. In some embodiments, the subject has male pattern baldness. In some embodiments, the subject has hair loss or hair thinning associated with cellular quiescence or dormancy of hair follicles. In some embodiments, the TRPV4 activating agent is administered intradermally or topically. In some embodiments, the TRPV4 activating agent is selected from the group consisting of: GSK1016790A; RN 1747; 5,6-EET; Apigenin; Bisandrographolide A; and Dimethylallyl pyrophosphate; or combinations thereof. In some embodiments, the TRPV4 activating agent is a small molecule activator GSK1016790A. In some embodiments, the TRPV4 activating agent is administered via microneedle injection, intraperitoneally, intradermally, topically, or orally. In some embodiments, the TRPV4 activating agent is administered intradermally by microneedle injection. In some embodiments, the therapeutically effective amount of the TRPV4 activating agent is an amount sufficient to induce telogen to anagen transition and hair follicle regeneration compared to a control or compared to the subject prior to being administered the TRPV4 activating agent. In some embodiments, a therapeutically effective amount of the TRPV4 activating agent is an amount sufficient to increase proliferation of hair follicle keratinocytes compared to a control or compared to the subject prior to being administered the TRPV4 activating agent. In some embodiments, a therapeutically effective amount of the TRPV4 activating agent is an amount sufficient to increase an amount of Ki67-positive K14-expressing hair follicle keratinocytes or stem cells compared to a control or compared to the subject prior to being administered the TRPV4 activating agent. In some embodiments, a therapeutically effective amount of the TRPV4 activating agent is an amount effective to: increase or upregulate expression of one or more anagen-promoting factors and decrease or downregulate expression of one or more anagen-inhibiting factors compared to a control or compared to the subject prior to being administered the TRPV4 activating agent. In some embodiments, the anagen-promoting factors are selected from Fgf7, Wnt16, or Nog; and/or the anagen-inhibiting factors are selected from Fgf18 or Bmp6. In some embodiments, a therapeutically effective amount of the TRPV4 activating agent is an amount sufficient to increase in ERK1/2 phosphorylation compared to a control or compared to the subject prior to being administered the TRPV4 activating agent. In some embodiments, the TRPV4 activating agent is administered in one treatment or multiple treatments over a time course of treatment. In some embodiments, the TRPV4 activating agent comprises dCas9 fused or interacts with a transcriptional activator, leading to activation of genetic expression of TRPV4, TRPV4 function, or TRPV4 activity (e.g., CRISPRa).

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

DETAILED DESCRIPTION

Figure 1:
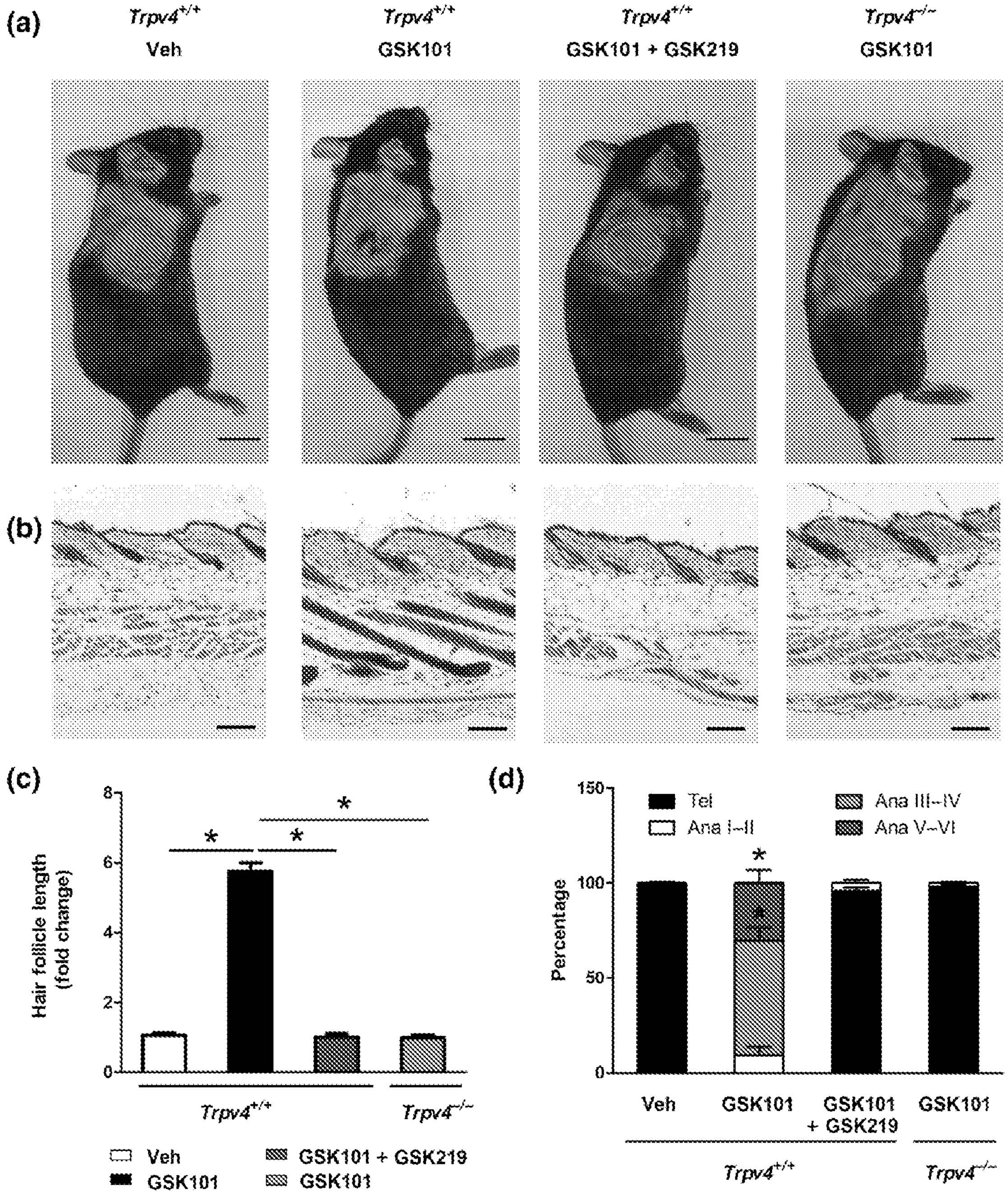
FIG. 1. TRPV4-mediated hair genesis. (a) Representative images showing hair growth in $Trpv4^{+/+}$ mice (n=10) intradermally injected with vehicle (Veh), 30 μM GSK1016790A (GSK101), GSK1016790A with 25 $mg \cdot kg^{-1}$ GSK2193874 (GSK219) pretreated and in $Trpv4^{-/-}$ mice (n=10) injected with GSK1016790A. Scale bar=1 cm. (b) Representative images of H&E staining showing back skin sections from $Trpv4^{+/+}$ mice treated with vehicle, GSK101, GSK101+GSK219 and $Trpv4^{-/-}$ mice with GSK1016790A injection (n=6). Scale bar=100 μm. (c) Quantification of hair follicle length in each group. (d) Stacked bars showing the percentage of hair follicles at the different stages of the hair cycle in each group (n=6). Data are expressed as mean±SEM. *$P<0.05$.

The present disclosure is based, at least in part, on the discovery that activating TRPV4 results in hair follicle (HF) regeneration. As shown herein, transient chemical activation of TRPV4 in the skin induces HF regeneration in mice.

It was previously known that bone morphogenetic protein signaling suppresses while overexpression of FGF7 and Noggin promotes hair follicle induction. These molecular cues originate from both hair follicle bulge and other types of dermal cells.

Here, it was discovered, that activation of TRPV4 is sufficient to regulate hair follicle telogen to anagen transition in mice. It was also discovered that TRPV4 activation disrupts the balance of anagen-promoting and inhibiting pathways that control hair follicle regeneration.

As such, this study suggests that keratinocyte-expressed TRPV4 is a potential target to promote hair follicle regeneration and TRPV4 is a novel target for the treatment of clinically relevant hair regeneration disorders.

New treatment for hair loss and alopecia through a single intradermal injection (e.g., a micro-injection) of a small molecule, selective TRPV4 agonist/activator, GSK1016790A (aka PF-4674114).

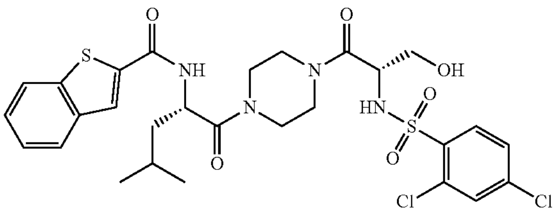

GSK1016790A

Current experimental evidence suggests that a single treatment may be sufficient for long-term and/or permanent restoration of hair growth. In addition, the current route of administration is thought to be novel.

It is envisioned to formulate to allow for topical administration of a TRPV 4 agonist. It is shown herein that a single injection results in new hair growth. There were no side effects observed with intradermal administration. It was shown that TRPV3 activation has the opposite effect (it is generally accepted that TRPV3 and TRPV4 have similar physiological effects).

As shown herein, it was demonstrated that a single intradermal injection of GSK1016790A is sufficient to induce telogen-anagen transition, hair follicle regeneration, and new hair growth in mice.

TRPV4 Activating Agent

One aspect of the present disclosure provides for targeting of TRPV4, its receptor, or its downstream signaling. The present disclosure provides methods of treating or preventing hair loss based on the discovery that transiently activating TRPV4 with an activating agent or TRPV4 activator (e.g., TRPV4 inducing agent, TRPV4 agonist).

As described herein, activators of TRPV4 (e.g., antibodies, fusion proteins, small molecules) can reduce or prevent hair loss or promote hair growth. A TRPV4 activating agent can be any agent that can activate TRPV4, upregulate TRPV4, or overexpress TRPV4.

As an example, a TRPV4 activating agent can induce, activate, or upregulate TRPV4 signaling.

For example, the TRPV4 activating agent can be one or more of the currently available TRPV4 activating agents, GSK1016790A; RN 1747; 5,6-EET; Apigenin; Bisandrographolide A; Dimethylallyl pyrophosphate; or combinations thereof. Undiscovered TRPV4 activating agents can be used as well.

As described herein, TRPV4 signals can be modulated (e.g., enhanced) using genome editing. Processes for genome editing are well known; see e.g. Aldi 2018 Nature Communications 9(1911). Except as otherwise noted herein, therefore, the process of the present disclosure can be carried out in accordance with such processes.

As an example, clustered regularly interspaced short palindromic repeats (CRISPR)/CRISPR-associated (Cas) systems are a new class of genome-editing tools that target desired genomic sites in mammalian cells. Type II CRISPR/Cas systems use Cas9 nuclease that is targeted to a genomic site by complexing with a synthetic guide RNA that hybridizes to a 20-nucleotide DNA sequence and immediately preceding an NGG motif recognized by Cas9 (thus, a $(N)_{20}$NGG target DNA sequence). This results in a double-strand break three nucleotides upstream of the NGG motif. The double-strand break instigates either non-homologous end-joining, which is error-prone and conducive to frame-shift mutations that knock out gene alleles, or homology-directed repair, which can be exploited with the use of an exogenously introduced double-strand or single-strand DNA repair template to knock in or correct a mutation in the genome.

Thus, genomic editing, for example, using CRISPR/Cas systems could be useful tools for therapeutic applications for treating hair loss to target cells by the addition of TRPV4 signals (e.g., activate (e.g., CRISPRa), upregulate, overexpress).

For example, the methods as described herein can comprise a method for altering a target polynucleotide sequence in a cell comprising contacting the polynucleotide sequence with a clustered regularly interspaced short palindromic repeats-associated (Cas) protein.

A TRPV4 activating agent can be any TRPV4 activating agent known in the art.

For example, a TRPV4 activating agent can be:

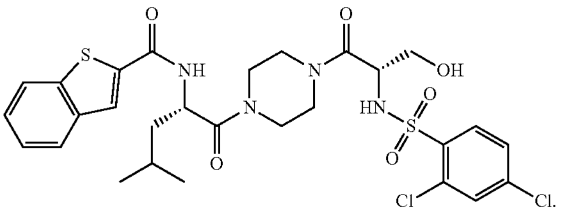

GSK1016790A

As another example, TRPV4 activating agent can be:

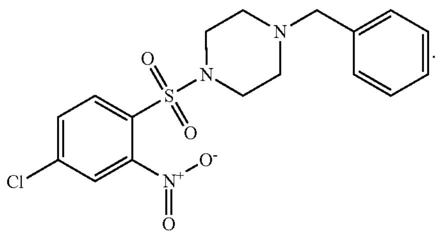

RN 1747

As another example, TRPV4 activating agent can be:

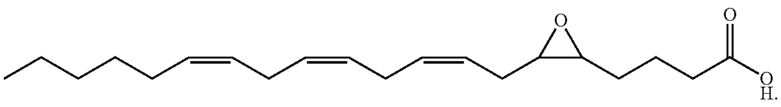

(±)5,6-epoxy-8Z,11Z,14Z-eicosatrienoic acid

As another example, TRPV4 activating agent can be:

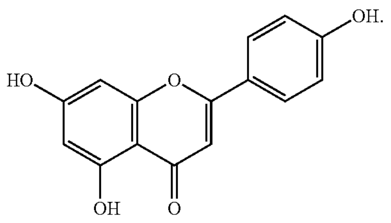

Apigenin

As another example, TRPV4 activating agent can be:

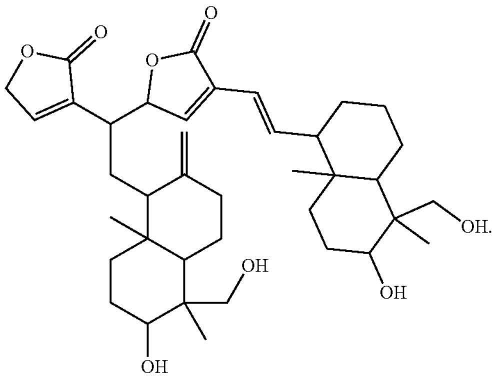

Bisandrographolide A

As another example, TRPV4 activating agent can be:

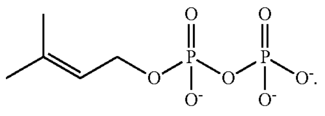

3-methylbut-2-en-1-yl disophate

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutically active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, microneedle injection, intratumoral, intranasal, inhalation (e.g., in an aerosol), implanted, intramuscular, intraperitoneal, intravenous, intrathecal, intracranial, intracerebroventricular, subcutaneous, intranasal, epidural, intrathecal, ophthalmic, transdermal, buccal, and rectal. In exemplary embodiments, the route of administration is intradermal, by microneedle injection, or topical. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic, or other physical forces.

Controlled-release (or sustained-release) preparations may be formulated to extend the activity of the agent(s) and reduce the dosage frequency. Controlled-release preparations can also be used to affect the time of onset of action or other characteristics, such as blood levels of the agent, and consequently, affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating, preventing, or reversing hair regeneration disorders or conditions (e.g., male pattern baldness, alopecia, telogen effluvium, thinning hair) in a subject in need of promotion of hair growth by administration of a therapeutically effective amount of a TRPV4 activating agent, so as to treat or prevent hair loss or promote hair follicle regeneration. Hair loss can be any loss of hair in an area that normally has hair or hair is thinning. For example, hair loss can be a condition, such as alopecia or baldness. As another example, hair loss can be alopecia areata, or a thinning of hair known as telogen effluvium. As another example, hair loss can be pattern hair loss that primarily affects the top and front of the scalp. In male-pattern hair loss (MPHL), the hair loss typically presents itself as either a receding front hairline, loss of hair on the crown (vertex) of the scalp, or a combination of both. Female-pattern hair loss (FPHL) typically presents as a diffuse thinning of the hair across the entire scalp. Less common causes of hair loss without inflammation or scarring can include the pulling out of hair, certain medications including chemotherapy, HIV/AIDS, hypothyroidism, and malnutrition including iron deficiency. Causes of hair loss that occurs with scarring or inflammation can include fungal infection, lupus erythematosus, radiation therapy, and sarcoidosis. Diagnosis of hair loss can be partly based on the areas affected.

A type of hair loss, alopecia areata, is an autoimmune disorder also known as "spot baldness" that can result in hair loss ranging from just one location (Alopecia areata monolocularis) to every hair on the entire body (Alopecia areata universalis). It is currently thought to be caused by hair follicles becoming dormant, but what triggers alopecia areata is not understood. In most cases the condition corrects itself, but it can also spread to the entire scalp (alopecia totalis) or to the entire body (alopecia universalis).

Methods described herein are generally performed on a subject in need thereof. A subject in need of the therapeutic methods described herein can be a subject having, diagnosed with, suspected of having, or at risk for developing hair regeneration disorders or conditions. A determination of the need for treatment will typically be assessed by a history, physical exam, or diagnostic tests consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and humans. For example, the subject can be a human subject.

Generally, a safe and effective amount of a TRPV4 activating agent is, for example, an amount that would cause the desired therapeutic effect in a subject while minimizing undesired side effects. In various embodiments, an effective amount of a TRPV4 activating agent described herein can substantially inhibit hair loss, slow the progress of hair loss, or limit the development of hair loss associated with a hair regeneration disorder or condition.

According to the methods described herein, administration can be parenteral, pulmonary, oral, topical, intradermal, microneedle injection, intramuscular, intraperitoneal, intravenous, intratumoral, intrathecal, intracranial, intracerebroventricular, subcutaneous, intranasal, epidural, ophthalmic, buccal, or rectal administration.

Here, tape stripping of the skin was used to facilitate entry of the agent, but other methods can be used to allow for enhanced entry of the agent into the skin (e.g., skin barrier disruption, microneedle (e.g., via roller or patch), laser, ultrasound, shaving, dermaplaning, abrasion, microderm abrasion, acid peel, chemical, patch, dermabrasion, electric, E-stim, Transcutaneous Electrical Nerve Stimulation (TENS), hydrodemabrasion, dermasanding, salabrasion, rotary surgical dermabrasion, etc.). Other methods can be used to increase skin permeation or dermal absorption such as an electric field, to enhance cutaneous administration of drugs. Any of these drug delivery systems or methods can be used in or for a topical or transdermal formulation. Any method or system described in the Review Braz. J. Pharm. Sci. 52 (03) September 2016 can be used.

When used in the treatments described herein, a therapeutically effective amount of a TRPV4 activating agent can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to substantially promote hair growth, promote hair follicle regeneration, inhibit hair loss, slow the progress of hair loss, or limit the development of hair loss associated with a hair regeneration disorder or condition.

The amount of a composition described herein that can be combined with a pharmaceutically acceptable carrier to produce a single dosage form will vary depending upon the subject or host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing, reversing, or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or a physician.

Administration of a TRPV4 activating agent can occur as a single event or over a time course of treatment. For example, a TRPV4 activating agent can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for hair regeneration disorders or conditions.

A TRPV4 activating agent can be administered simultaneously or sequentially with another agent, such as an antibiotic, an anti-inflammatory, or another hair loss prevention agent or a hair growth-promoting agent. For example, a TRPV4 activating agent can be administered simultaneously with another agent, such as a hair loss prevention agent or a hair growth-promoting agent, an antibiotic, or an anti-inflammatory. Simultaneous administration can occur through the administration of separate compositions, each containing one or more of a TRPV4 activating agent, hair loss prevention agent or hair growth-promoting agent, an antibiotic, an anti-inflammatory, or another agent. Simultaneous administration can occur through the administration of one composition containing two or more of a TRPV4 activating agent, hair loss prevention agent or hair growth-promoting agent, an antibiotic, an anti-inflammatory, or another agent. A TRPV4 activating agent can be administered sequentially with a hair loss prevention agent or hair growth-promoting agent, an antibiotic, an anti-inflammatory, or another agent. For example, a TRPV4 activating agent can be administered before or after administration of an antibiotic, an anti-inflammatory, or another agent.

The compositions and treatments can be used in combination with other hair loss (e.g., alopecia) treatment or hair growth-promoting treatment, such as Rogaine (J&J), Minoxidil, loniten (Pfizer), Finasteride, Proscar/Propecia (Merck), Viviscal vitamin supplement, Follica (Puretech), Replicel RCH-01 (Shiseido), HSC (Histogen), FOL-005 (Follicum), Kerastem, ATI-50001/02 (Aclaris), or combinations thereof.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, microneedle injection, intratumoral, intranasal, inhalation (e.g., in an aerosol), implanted, intramuscular, intraperitoneal, intravenous, intrathecal, intracranial, intracerebroventricular, subcutaneous, intranasal, epidural, intrathecal, ophthalmic, transdermal, buccal, and rectal.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 μm), nanospheres (e.g., less than 1 μm), microspheres (e.g., 1-100 μm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency; improve the taste of the product; or improve the shelf life of the product.

The concentration of the agent can be between about 1 μM and about 30 μM. The agent can be administered once or over the time course of a treatment regime (such as once a week, once a month, etc. for a period of time, such as over the course of a month or year, etc. or for an amount of time sufficient to result in desired hair growth).

Kits

Also provided are kits. Such kits can include an agent or composition described herein and, in certain embodiments, instructions for administration. Such kits can facilitate the performance of the methods described herein. When supplied as a kit, the different components of the composition can be packaged in separate containers and admixed immediately before use. Components include, but are not limited to TRPV4 activating agents or pharmaceutically acceptable carriers or excipients. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water or sterile saline each of which has been packaged under a neutral non-reacting gas, such as nitrogen. Ampules may consist of any suitable material, such as glass, organic polymers, such as polycarbonate, polystyrene, ceramic, metal, or any other material typically employed to hold reagents. Other examples of suitable containers include bottles that may be fabricated from similar substances as ampules and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or another substrate, and/or may be supplied as an electronic-readable medium or video. Detailed instructions may not be physically associated with the kit; instead, a user may be directed to an Internet website specified by the manufacturer or distributor of the kit.

Compositions and methods described herein utilizing molecular biology protocols can be according to a variety of standard techniques known to the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application, or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Transient Stimulation of Trpv4-Expressing Keratinocytes Promotes Hair Follicle Regeneration in Mice The following example describes the acute activation of TRPV4 induced hair follicle (HF) regeneration. It was shown herein that transient chemical activation of TRPV4 in the skin induces hair follicle (HF) regeneration in mice, which can provide an effective therapeutic strategy for the treatment of hair loss and alopecia.

Abstract

Background and purpose: Hair follicle telogen to anagen transition results in a break in cellular quiescence of the hair follicle stem cells, which subsequently promotes hair follicle regeneration. Many critical molecules and signaling pathways are involved in hair follicle cycle progression. Transient receptor potential vanilloid 4 (TRPV4) is a polymodal sensory transducer that regulates various cutaneous functions under both normal and disease conditions. However, the role of TRPV4 in hair follicle regeneration in vivo remains incompletely understood.

Experimental approach: Using adult C57BL/6J mice, keratinocyte (K14$^{Cre}$ Trpv4$^{f/f}$) and macrophage (Cx3cr1$^{Cre}$; Trpv4$^{f/f}$) Trpv4 conditional knockout (cKO) mice, Trpv4$^{-/-}$ mice, the effect of a single intradermal injection of GSK1016790A, a potent and selective small molecule TRPV4 activating agent or activator, on hair follicle regeneration was investigated. Chemical cues and signal molecules involved in hair follicle cycle progression were measured by immunofluorescence staining, quantitative RT-PCR, and western blotting.

Key results: Here, it is shown that a single intradermal injection of a TRPV4 activating agent, GSK1016790A, is sufficient to induce telogen to anagen transition and hair follicle regeneration in mice by increasing the expression of the anagen-promoting growth factors and down-regulating the expression of growth factors that inhibit anagen. The action of GSK1016790A relies largely on the function of TRPV4 in the skin and involves activation of downstream ERK signaling.

Conclusion and implications: These results show that transient chemical activation of TRPV4 in the skin can induce hair follicle regeneration in mice, which can provide an effective therapeutic strategy for the treatment of hair loss and alopecia.

INTRODUCTION

The hair follicle is the most prominent mini-organ found in the skin. It is composed of three main components: the outer root sheath, the inner root sheath, and the hair shaft. The hair follicle cyclically transforms from rapid growth (anagen) to apoptosis-driven regression (catagen), and last, to relative quiescence (telogen) phases (Muller-Rover et al., 2001; Oshima, Rochat, Kedzia, Kobayashi, & Barrandon, 2001). Many critical molecules and signaling pathways are involved in these distinct phases of hair follicle cycle progression. The quiescence of hair follicle stem cells during telogen is largely maintained by bone morphogenetic proteins (BMPs) derived from both bulge cells and many other types of dermal cells. For instance, the subcutaneous adipocytes and dermal fibroblasts produce BMP-2A and BMP-2B that inhibit anagen (Plikus et al., 2008) and the inner bulge layer secrets high levels of VG-1-related protein (BMP-6) and FGF18 that suppress the proliferation of hair follicle keratinocytes (Hsu, Pasolli, & Fuchs, 2011). On the other hand, dermal papilla-derived anagen-promoting FGF7 and Noggin are elevated when the hair follicle progresses from early telogen to late telogen. Moreover, Noggin expression is rapidly induced following the activation of bone morphogenetic protein receptors and therefore acts as an effective feedback antagonist against bone morphogenetic protein signaling (Gazzerro, Gangji, & Canalis, 1998; Ito, Akiyama, Shigeno, & Nakamura, 1999).

Transient receptor potential (TRP) channels are versatile players in the skin and regulate various cutaneous functions under both normal and disease conditions besides serving as molecular sensors for detecting many distinct sensory modalities (Nilius & Szallasi, 2014). Many TRP channels, especially TRP vanilloid 3 (TRPV3) and TRP vanilloid 4 (TRPV4) are extensively expressed in the skin-resident cells and play critical roles in skin physiology and diseases (Caterina & Pang, 2016; Luo & Hu, 2014; Toth, Olah, Szollosi, & Biro, 2014). TRPV3 plays important roles in hair morphogenesis in mice (Cheng et al., 2010) and gain-of-function TRPV3 mutations in humans cause Olmsted syndrome which is associated with severe chronic itching and skin disorders (Lin et al., 2012). Moreover, TRPV3 was reported to play different roles in hair follicle cycling (Borbiro et al., 2011; Imura et al., 2007). TRPV4 is a polymodal sensory transducer that integrates a variety of thermal, mechanical, and chemical stimuli including warmth (27-35° C.), hypo-osmotic stimulation, and many inflammatory metabolites (Nilius & Szallasi, 2014; Voets, 2014), contributing to pain sensation, epidermal barrier homeostasis and the formation of tight junctions (Denda, Sokabe, Fukumi-Tominaga, & Tominaga, 2007; Kida et al., 2012; Mamenko, Zaika, Boukelmoune, O'Neil, & Pochynyuk, 2015; Sokabe, Fukumi-Tominaga, Yonemura, Mizuno, & Tominaga, 2010; Sokabe & Tominaga, 2010). Our previous study further demonstrated that TRPV4 is highly expressed by both skin keratinocytes and dermal macrophages and contributes to the pathogenesis of both allergic and non-allergic chronic itch in mice (Luo et al., 2018). Although a recent study showed that activation of TRPV4 induces apoptosis and drives early catagen transition in human hair follicles, which inhibits human hair growth ex vivo (Szabo et al., 2019), the role of TRPV4 in hair follicle regeneration in vivo remains unclear.

In the present study, it was demonstrated that transient chemical activation of TRPV4 is sufficient to trigger hair follicle regeneration through regulating hair follicle telogen to anagen transition in wild-type (wt) but not TRPV4 KO mice. Mechanistically, TRPV4 activation disrupts the balance of anagen-promoting and inhibiting signaling pathways that control hair follicle regeneration. Moreover, TRPV4-mediated response requires ERK signaling pathway in keratinocytes. These findings identify the keratinocyte-expressed TRPV4 as an effective promoter of hair follicle regeneration in mice.

Methods

Animals

Adult (7-10 weeks, around 20-g body weight) male and female C57BL/6J mice (Jackson Laboratories, Ellsworth, ME, USA), $K14^{Cre}$ (Jackson Laboratories), $Cx3cr1^{Cre}$ (Jackson Laboratories), and $Trpv4^{-/-}$ (provided by Masashi Imai, Jichi Medical School, Tochigi, Japan) (Suzuki, Mizuno, Kodaira, & Imai, 2003) were used in this study. To generate the $Trpv4^{f/f}$ mice, three of the properly targeted ES cell clones were obtained from the KOMP Repository and used for blastocyst injections and one clone led to high contribution chimeras that produced germline transmitted offspring as assayed by black coat color.

This chimera line was then mated to FLPo mice (Jackson Laboratories) to remove the neomycin cassette and generate heterozygous $Trpv4^{f/+}$ mice, which were subsequently crossed with $K14^{Cre}$ and $Cx3cr1^{Cre}$ to generate both $Cre^{+}$ and $Cre^{-}$ $Cx3cr1^{Cre}$; $Trpv4^{f/f}$ and $K14^{Cre}$; $Trpv4^{f/f}$ mice, respectively. All mice were housed under a 12:12-h light/dark cycle with food and water provided ad libitum. All animal care and experimental procedures were performed using protocols approved by the Animal Studies Committee at Washington University School of Medicine and were in accordance with the guidelines provided by the National Institutes of Health. All mice were randomly allocated to different experimental groups by the lab members who were blinded to the experimental design. Data analysis was also performed in a manner completely blind to experimental groups. At the end of the experiments, mice were killed by $CO_2$ asphyxia. Animal studies are reported in compliance with the ARRIVE guidelines (Kilkenny, Browne, Cuthill, Emerson, & Altman, 2010; McGrath & Lilley, 2015) and with the recommendations made by the *British Journal of Pharmacology.*

Animal Treatment

The second telogen of C57BL/6J mice starts at day 49 after birth and it will last around 5 weeks (Muller-Rover et al., 2001). On day 48 after birth, the mice were shaved. On day 49 after birth, wt and $Trpv4^{-/-}$ mice were intradermally injected with 30-μM GSK1016790A (GSK101, a selective TRPV4 agonist) (50 μl), which is diluted in saline from the 100 mM stock solution. GSK2193874 (GSK219, a selective TRPV4 antagonist) (25 $mg\cdot kg^{-1}$, 200 μl dilution in saline from 50 $mg\cdot ml^{-1}$ stock solution) (Thorneloe et al., 2012) or PD98059 (10 $mg\cdot kg^{-1}$, 200 μl dilution in saline from 37.5 $mg\cdot ml^{-1}$ stock solution) was applied through intraperitoneal injection on day 48 after birth or 1 hour prior to GSK1016790A injection. Insulin syringes with 30-G needle (UltiCare) were used for intradermal injection and 1-ml Sub-Q syringes with 26-G needle (BD) were used for intraperitoneal injection. Seventeen days after GSK1016790A injection, the mice were killed and the skin samples of the injection area were collected for analysis. In mice with newly generated hair, generally, there was a small patch of skin with dark color and longer hair shaft at the injection sites compared with that in the surrounding area.

Histology, Immunofluorescence Staining

Dorsal skin samples were fixed overnight at 4° C. in Zamboni's fixative (2% paraformaldehyde, 15% [v/v] saturated picric acid, 0.1-M PB, pH 7.3), dehydrated in ethanol, embedded in paraffin and sectioned at 10 μm. Haematoxylin and eosin (H&E) staining was performed according to standard protocols to analyze the hair follicle cycle stages as described, including the length of the hair follicle, the size, and location of dermal papilla and the position of the hair shaft and the inner root sheath (Muller-Rover et al., 2001). For immunofluorescence detection, sections were deparaffinized, rehydrated, and subjected to antigen retrieval in 10-mM citrate buffer (pH 6.0). After blocking, sections were stained with primary antibody against Ki67 (1:1,000; Thermo Fisher Scientific, Cat #PA1-29503, RRID: AB_1955602), phosphop-p44/42 MAPK (1:200; Cell Signaling Technology, Cat #4370S, RRID: AB_2315112), p44/42 MAPK (1:1,000; Cell Signaling Technology, Cat #4695, RRID: AB_390779), keratin 14 (1:1,000; BioLegend, Cat #, RRID: AB_2616962) and keratin 15 (1:1,000; BioLegend, Cat #833901, RRID: AB_2564970) at 4° C. overnight in a humid chamber, followed by incubation for 1 h at room temperature (RT) with Cy3-conjugated secondary antibody (1:500; Jackson ImmunoResearch, Cat #111-005-003, RRID: AB_2337913) and Alexa Fluor 488-conjugated secondary antibody (1:500; Jackson ImmunoResearch, Cat #703-005-155, RRID: AB_2340346). Nuclei were stained with DAPI (SouthernBiotech). The Immuno-related procedures used comply with the recommendations made by the *British Journal of Pharmacology* Alexander et al., 2018.

Quantitative RT-PCR

For real-time PCR, skin sample was collected 24 h after GSK1016790A injection. Total RNA was extracted from mouse skin tissue using RNeasy kit (Qiagen, Germantown, MD, Germany) according to the manufacturer's instructions. RNA was treated with DNase I (Invitrogen, Carlsbad, CA, USA), and the cDNA was synthesized in vitro using ThermoScript® RT-PCR System kit (Invitrogen). Primers used for PCR are listed in TABLE 1. Reactions were carried out in a volume of 20 μl per reaction containing 10-μl SYBR Green master mix (2×) (Roche, Indianapolis, IN, USA), 0.5-μl cDNA, 1.2-μl 5-μM primer mix, and 8.3-μl water using StepOnePlus real-time PCR system (Applied Biosystems, Foster City, CA, USA). Relative expression of genes was normalized to GAPDH and calculated using the $2^{-\Delta\Delta ct}$ methods.

TABLE 1

Real-time RT-PCR primer pairs.

| Gene | SEQ ID NO: | Forward (5'-3') | SEQ ID NO: | Reverse (5'-3') |
|---|---|---|---|---|
| Bmp6 | 1 | AGCACAGAGACTCTGACCTA TTTTTG | 2 | CCACAGATTGCTAGTTGCT GTGA |
| Fgf7 | 3 | TTGTGGCAATCAAAGGGGTG | 4 | CCTCCGCTGTGTGTCCAT TTAGC |
| Fgf18 | 5 | GAATTCTACCTGTGTATGAA CCGAAA | 6 | TGAACACGCACTCCTTGC TAGT |
| Wnt16 | 7 | AGAGTGCAACCGGACATCAG | 8 | CGTAGCAGCACCAGATAA ACTT |
| Nog | 9 | CCTGGTGGACCTCATCGAA | 10 | CAGCGTCTCGTTCAGATC CTT |
| Gapdh | 11 | AGGTCGGTGTGAACGGATTT G | 12 | TGTAGACCATGTAGTTGA GGTCA |

Western Blotting

The skin was lysed in RIPA lysis and extraction buffer (Thermo Fisher Scientific, USA). Following cell protein quantitation, 10 μg of protein per sample were subjected to 12% SDS-PAGE. The proteins separated on the SDS-PAGE gel were transferred to a PVDF membrane (Millipore Corp., Billerica, MA, USA), which was blocked for 1 h at RT. The membrane was then incubated overnight at 4° C. with monoclonal antibodies against R-actin (1:5,000; Sigma-Aldrich, Cat #A5441, RRID: AB_476744) or phosphop-p44/42 MAPK (1:200; Cell Signaling Technology, Cat #4370S, RRID: AB_2315112) and p44/42 MAPK (1:1,000; Cell Signaling Technology, Cat #4695, RRID: AB_390779) followed by incubation with a secondary antibody conjugated with HRP. Immunoreactive bands were visualized by an enhanced chemiluminescence (ECL) system.

Data and Statistical Analysis

The data and statistical analysis comply with the recommendations of the *British Journal of Pharmacology* on experimental design and analysis in pharmacology (Curtis et al., 2018). Data are expressed as the mean±SEM. No statistical power calculation was conducted before the study. Sample sizes subjected to statistical analysis at least 5 animals per group (n=5), where n=number of independent values. The differences in hair follicle cycling were compared by Fisher's exact test. The significance was determined by one-way ANOVA for comparisons among three or more groups and Student's unpaired t-test for comparisons between two groups with GraphPad Prism 7 (GraphPad Software Ltd., San Diego, CA, USA, RRID: SCR_002798). A value of $P<0.05$ was considered significantly different. The post hoc tests were conducted only if F in ANOVA achieved $P<0.05$ and there was no significant variance inhomogeneity.

Materials

PD98059 was from Cell Signaling Technology (Danvers, USA). GSK1016790A was from Sigma-Aldrich Inc. (St. Louis, MO, USA). GSK2193874 was purchased from Tocris (Minneapolis, USA). Stock solutions of drugs were made in DMSO and diluted to working concentrations in saline immediately before use.

Nomenclature of Targets and Ligands

Key protein targets and ligands in this article are hyperlinked to corresponding entries in http://www.guidetopharmacology.org, the common portal for data from the IUPHAR/BPS Guide to PHARMACOLOGY (Harding et al., 2018) and are permanently archived in the Concise Guide to PHARMACOLOGY 2019/20 (Alexander et al., 2019).

Results

Figure 6:
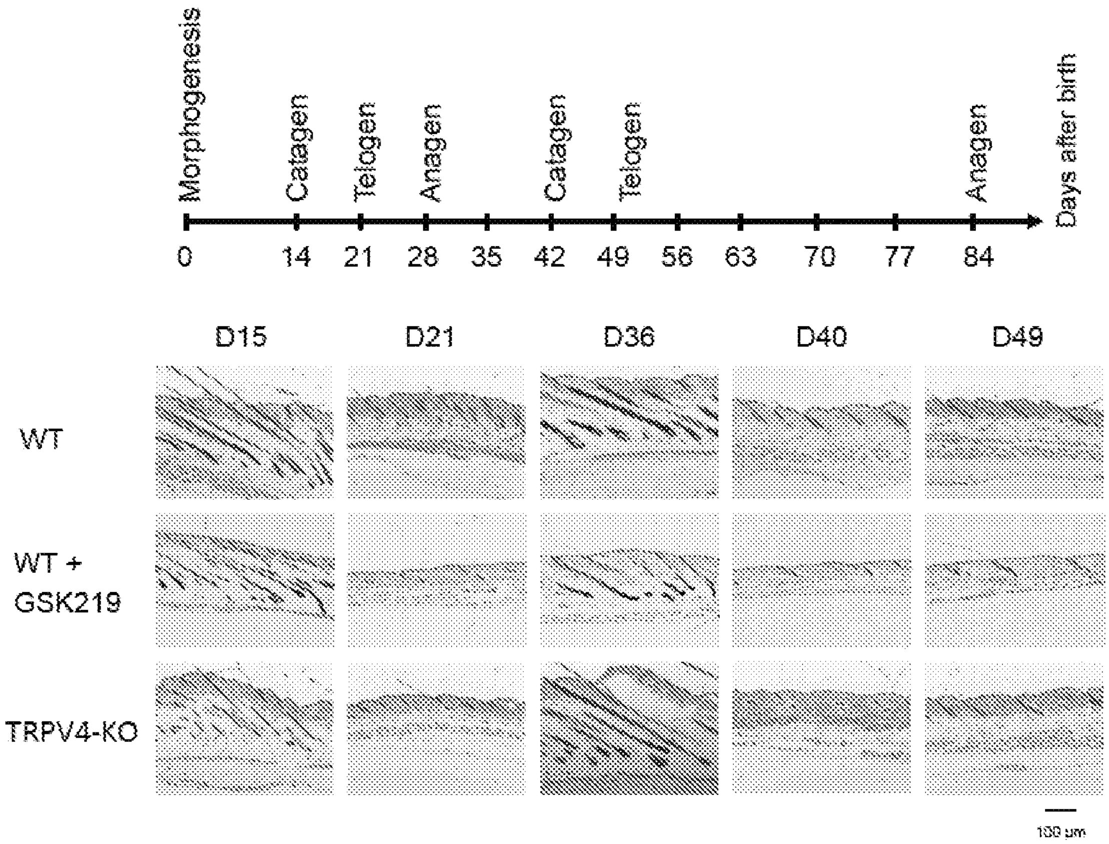
FIG. 6. Top: hair growth cycle in mice. Bottom: representative images of hematoxylin and eosin (H&E) staining of back skin sections from $Trpv4^{+/+}$ mice, $Trpv4^{+/+}$ mice treated with GSK219 and $Trpv4^{-/-}$ mice on Day 15, 21, 36, 40, 49. Scale bar=100 μm.

TRPV4 Activation by a Small Molecule Activator Induces Hair Follicle Regeneration To confirm whether activation of TRPV4 could affect the normal hair follicle cycling in mice, it was first examined whether genetic ablation of TRPV4 function affects general hair follicle cycling. It was found that there was no difference in the hair follicle cycling between the TRPV4 KO mice and their wild type (wt) littermates (FIG. 6). Moreover, pharmacological inhibition of TRPV4 function with the TRPV4 antagonist GSK2193874 had no effect on the normal transition of first telogen to second anagen (FIG. 6). These results suggest that TRPV4 is not involved in general hair follicle cycling under normal conditions.

Figure 7:
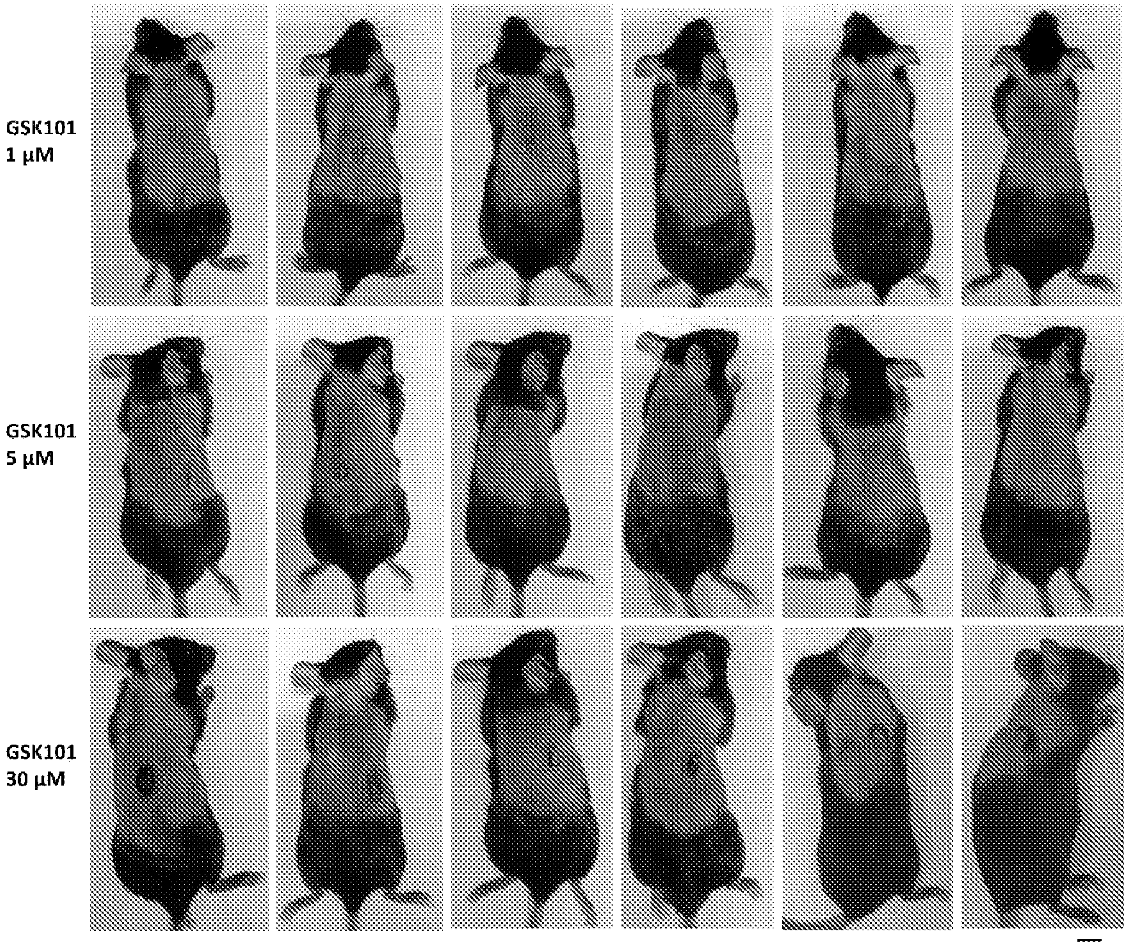
FIG. 7. Representative images showing hair growth in 7-week-old $Trpv4^{+/+}$ mice 17 days after injection with 1, 5, or 30 μM, GSK1016790A (GSK101). Scale bar=1 cm.

To further investigate the function of TRPV4 in hair follicles, a single intradermal injection of GSK1016790A, a potent and selective small molecule TRPV4 activating agent or activator was performed (Thorneloe et al., 2008) into the back skin of 7-week-old wt mice, where the hair follicles were in telogen, that is the entire hair follicle resides in the upper dermis and is associated with ball-shaped dermal papilla (Muller-Rover et al., 2001; Paus & Cotsarelis, 1999). Surprisingly, 17 days after the GSK1016790A injection, the newly generated hair coat could be clearly observed at the injection site in a dose-dependent manner but not in mice with vehicle injection (FIG. 1*a* and FIG. 7). After GSK1016790A injection, the hair follicles were elongated by more than fourfold with the bulbs resided in the deep subcutis, reminiscent of anagen phase (FIG. 1*b*, FIG. 1*c*). Furthermore, most of the hair follicles had entered anagen Ill-VI phases after GSK1016790A injection, whereas most hair follicles were in the telogen or anagen I phase after vehicle treatment (FIG. 1*d*). Importantly, the GSK1016790A-induced hair regeneration was completely abolished by pretreatment with TRPV4 antagonist GSK2193874. Moreover, the GSK1016790A-induced hair regeneration was completely absent from the global TRPV4 KO mice (FIG. 1*a*-FIG. 1*c*). Taken together, these results suggest that a single intradermal injection of GSK1016790A is sufficient to promote hair follicle regeneration. Given that GSK1016790A selectively activates TRPV4, it is conceivable that this receptor is the sole mediator of GSK1016790A-induced hair follicle transition from telogen to anagen.

Figure 2:
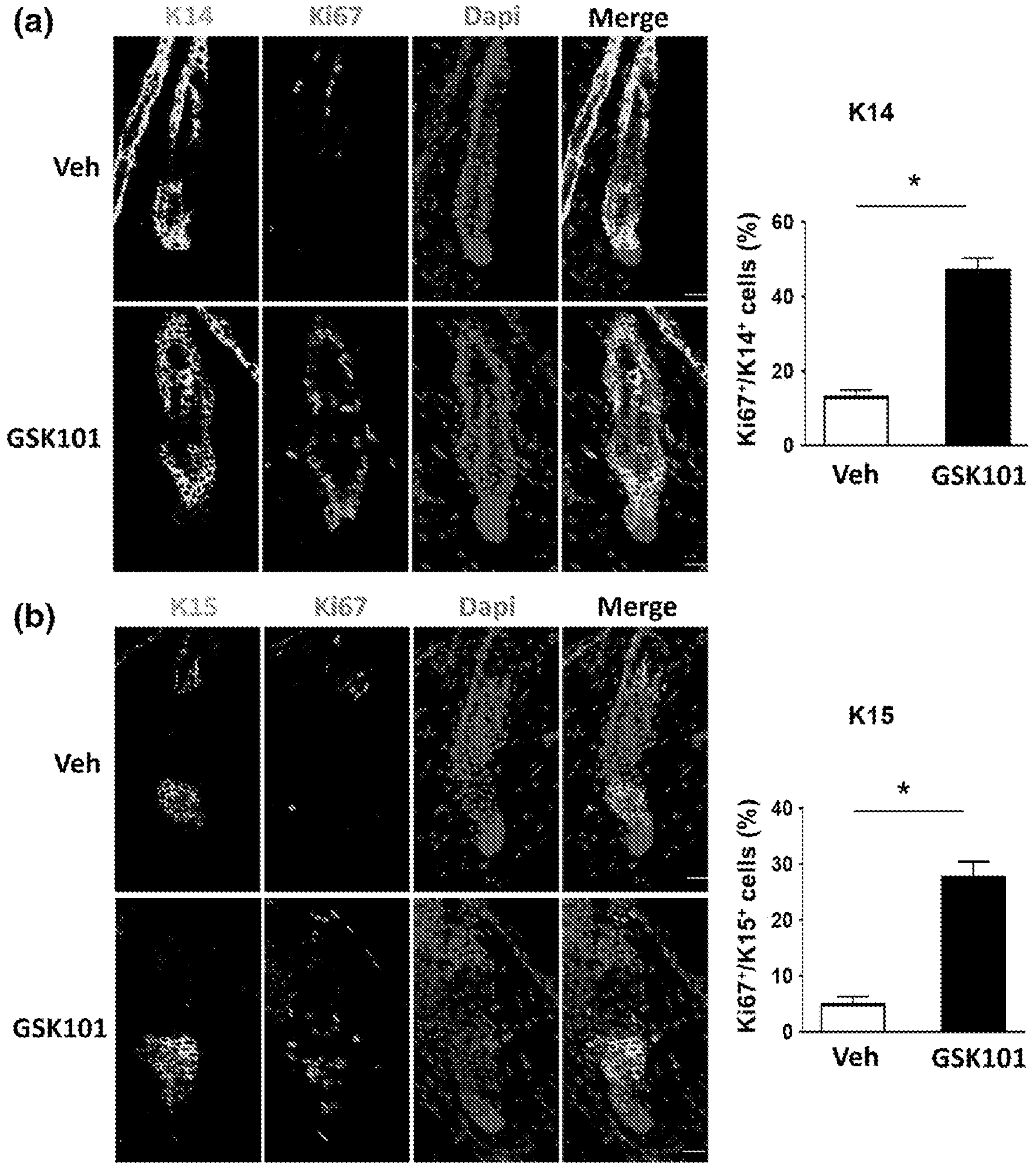
FIG. 2. TRPV4 activation induces hair follicle keratinocytes proliferation. Representative immunofluorescent images of back skin sections from $Trpv4^{+/+}$ mice (n=6) at 48 h after injection with vehicle (Veh) or GSK1016790A (GSK101) reveal an increase of Ki67-positive cells in K14-positive (a) and K15-positive (b) cells. Bar charts on the right show the percentage of Ki67-positive cells. Data are mean±SEM. Scale bar=100 μm. *P<0.05.

TRPV4 Activation by GSK1016790A Increases Proliferation of Hair Follicle Keratinocytes Since the early stage of hair follicle development is characterized by intensive proliferative activity (Schmidt-Ullrich & Paus, 2005), it was examined if a single intradermal injection of GSK1016790A affects the proliferative activity of hair follicle keratinocytes at the site of injection using Ki67 staining. Indeed, the number of Ki67-positive K14-expressing hair follicle keratinocytes was significantly increased in comparison with that in mice injected with vehicle only (FIG. 2*a*). Furthermore, an increased number of Ki67-positive K15-expressing hair follicle stem cells were also observed in the bulge of the mice subjected to GSK1016790A injection, suggesting that hair follicle stem cell proliferation could be involved in GKS101-induced hair follicle regeneration (FIG. 2*b*). Therefore, transient chemical activation of TRPV4 in the skin can promote proliferation of keratinocytes and stem cells in telogen.

TRPV4 Activation Shifts the Balance of Chemical Cues that Inhibit or Promote Activity of Hair Follicle Stem Cells Multiple signaling pathways including these for Wnt/β-catenin, bone morphogenetic protein and FGFs are critically involved in hair follicle development and cycling (Hsu et al., 2011; Plikus et al., 2008). From early to late telogen, the expression of several hair germ activation cues is increased, including FGF7 and bone morphogenetic protein inhibitor Noggin, while the BMPs are down-regulated, which facilitates activation of the hair follicle stem cells (Greco et al., 2009; Plikus et al., 2008). Moreover, Wnt signaling in dermal papilla also plays an important role in hair germ activation (Enshell-Seijffers, Lindon, Kashiwagi, & Morgan, 2010; Greco et al., 2009; Kandyba et al., 2013). Therefore, both an increase in expression of anagen-promoting chemical cues and a decrease in expression of anagen-inhibiting growth factors induce hair follicle telogen to anagen transition.

Figure 3:
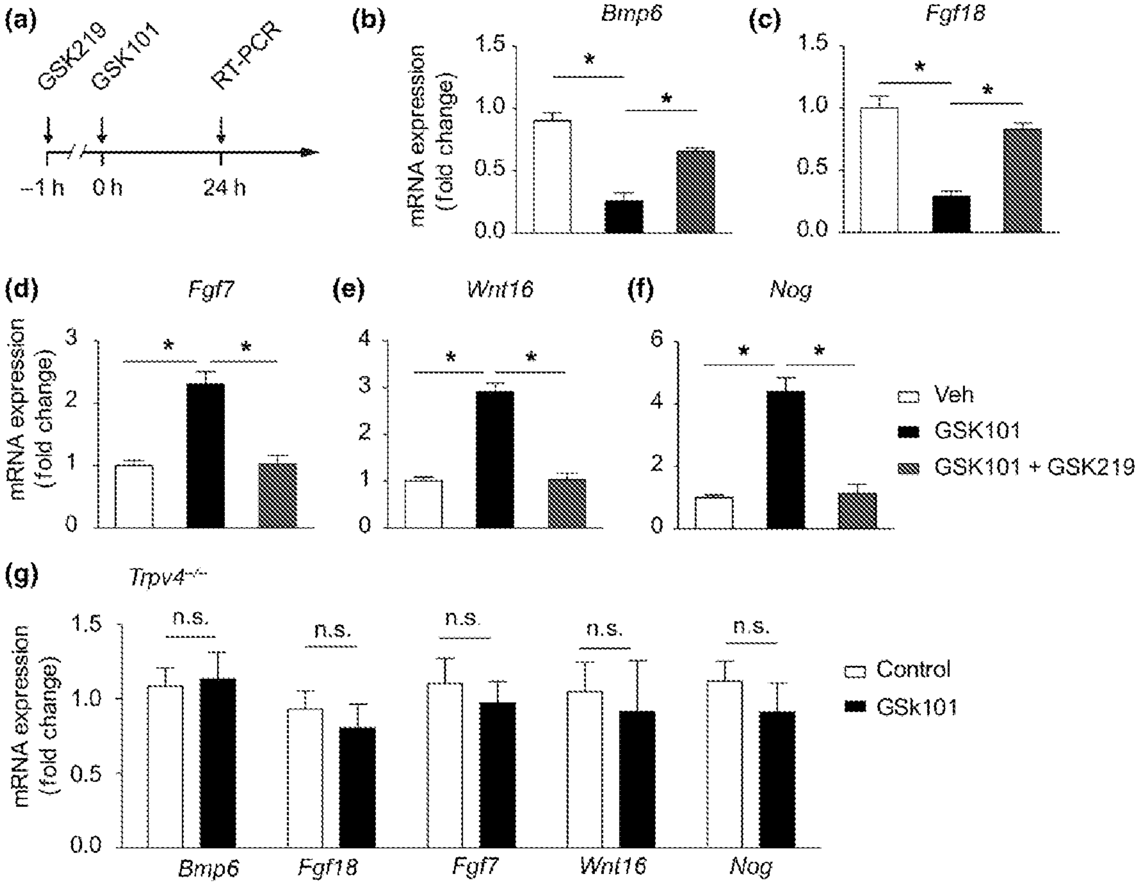
FIG. 3. TRPV4 activation disrupts the balance of hair follicle stem cell inhibiting and activating factors. (a) Schematic diagram illustrates experimental protocol. Quantitative RT-PCR data obtained from whole skin lysates of $Trpv4^{+/+}$ mice (n=5) 24 h after indicated treatments showing gene expression for Bmp6 (b), Fgf18 (c), Fgf7 (d), Wnt16 (e) and Nog (f). (g) $Trpv4^{-/-}$ mice (n=5) were intradermally injected with vehicle (Veh) or 30-μM GSK1016790A (GSK101). As for the $Trpv4^{+/+}$ mice, the expression of target mRNAs was examined 24 h after GSK1016790A injection. Data are expressed as mean±SEM. *P<0.05; n.s., non-significance.

It was thus tested if TRPV4-mediated hair follicle regeneration involves changes in the expression of signaling molecules that either promote or inhibit hair follicle telogen to anagen transition by using real-time RT-PCR 24 h after GSK1016790A injection (FIG. 3*a*). Indeed, GSK1016790A treatment resulted in a significant decrease in the mRNA transcripts of both Bmp6 and Fgf18, while markedly increased the mRNA transcripts of Fgf7, Wnt16, and Nog (FIG. 3*b*-FIG. 3*f*). Both pharmacological inhibition by GSK2193874 and genetic ablation of the TRPV4 function significantly attenuated the effect of GSK1016790A (FIG. 3*b*-FIG. 3*g*), suggesting that TRPV4 is responsible for GSK1016790A-induced changes in expression of these signaling molecules.

Figure 4:
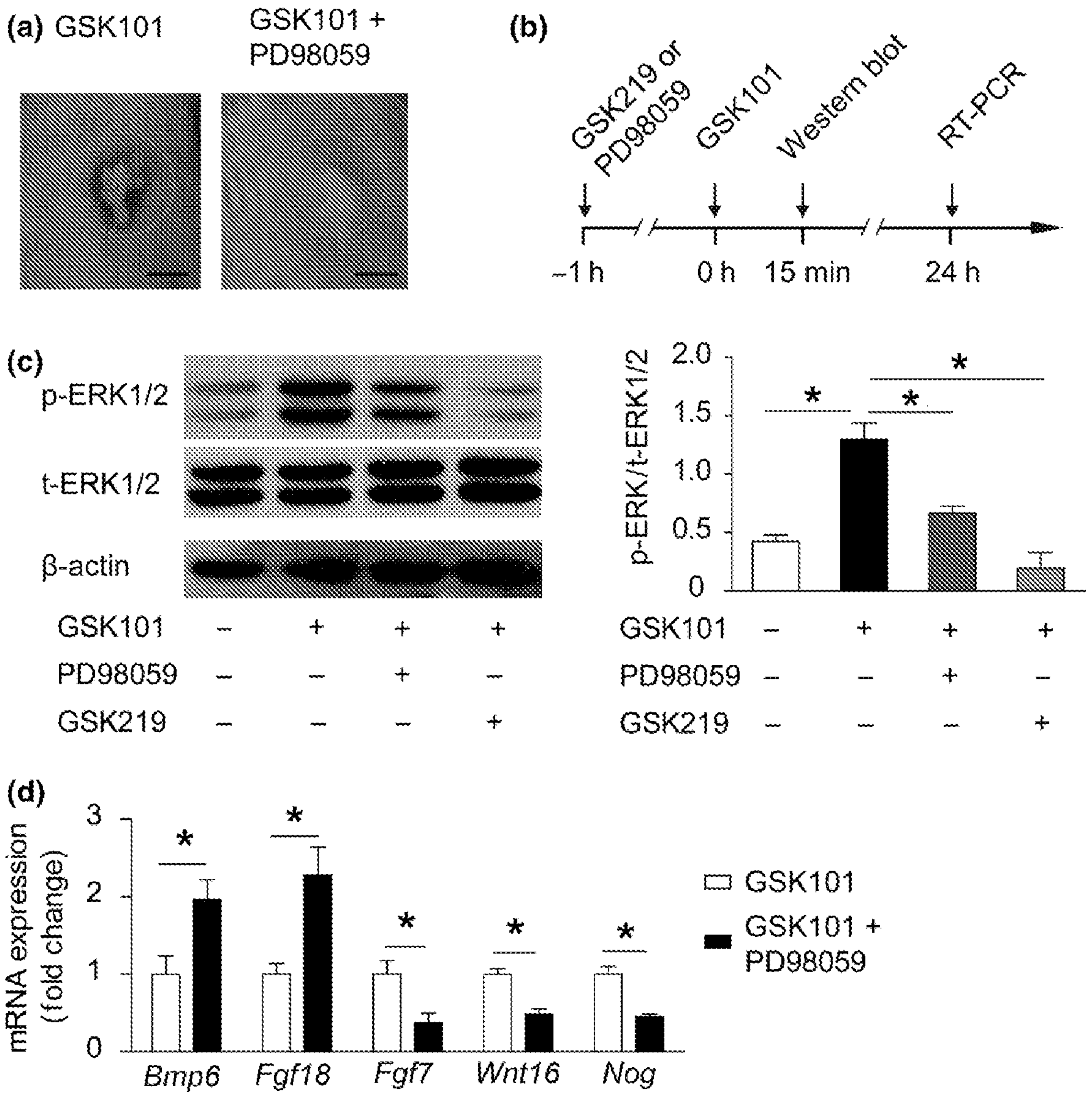
FIG. 4. TRPV4-mediated hair regeneration requires ERK signaling. (a) Representative images showing new hair growth in $Trpv4^{+/+}$ mice injected with 30-μM, GSK1016790A (GSK101) in the absence (n=5) or presence (n=5) of PD98059. Scale bar=0.5 cm. (b) Schematic diagram illustrates the experimental protocol. (c) Western blot data obtained from whole skin lysates subjected to different treatments using antibodies against phosphorylated ERK (p-ERK), total ERK (t-ERK), or R-actin (n=5, respectively). Bar charts on the right illustrate the quantification of p-ERK expression. Data are expressed as mean±SEM. (d) Quantitative RT-PCR data obtained from whole skin lysates showed that PD98059 pretreatment reversed the GSK1016790A-induced disruption of hair follicle stem cell inhibiting and activating factors. Data are mean±SEM and normalized to the PD98059 presence group. Five independent experiments were performed. *P<0.05.
Figure 8:
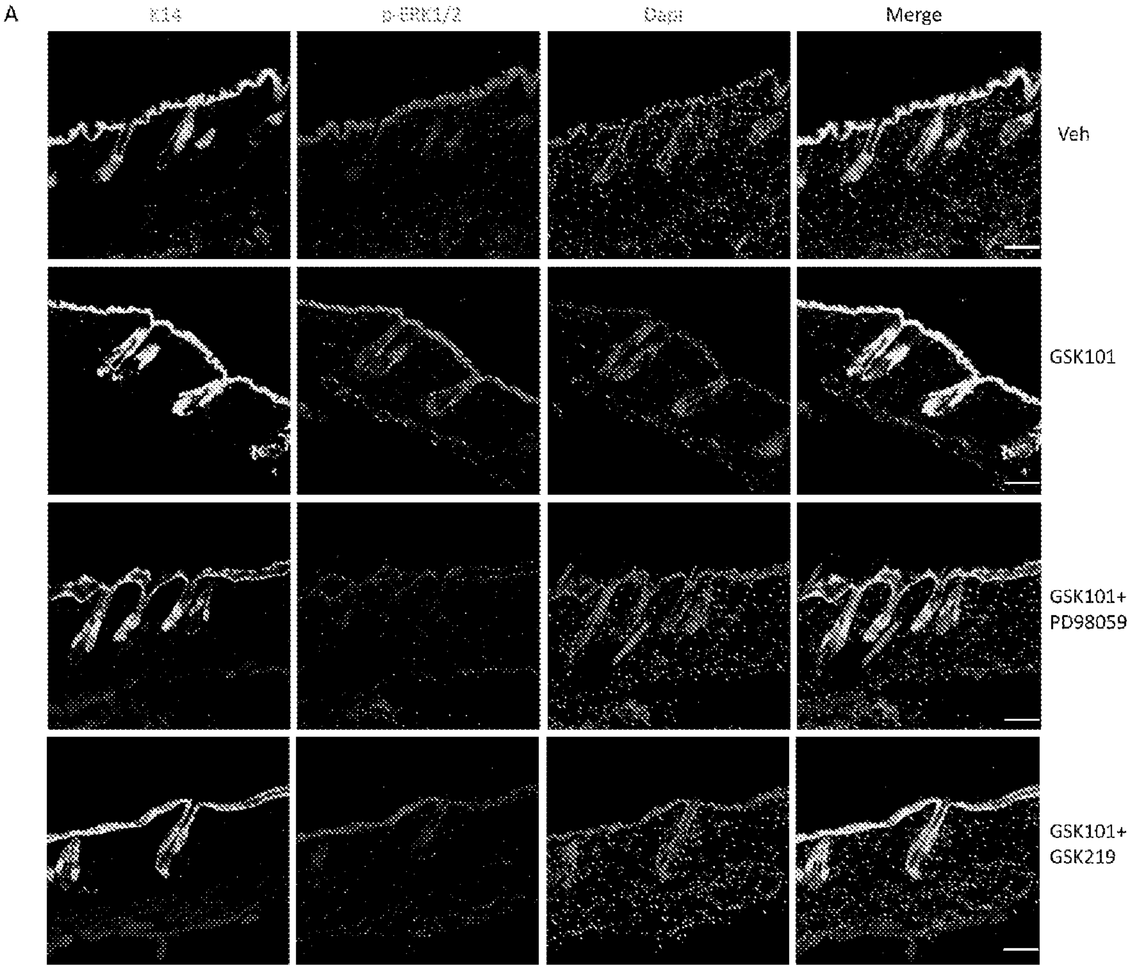
FIG. 8. TRPV4-dependent ERK signaling. 7-week-old $Trpv4^{+/+}$ mice were subjected to a single intradermal injection of GSK1016790A (GSK101) one hour after intraperitoneal injection of PD98059 or GSK219. The skin preparations at the injection sites were harvested 15 minutes after GSK101 injection. Representative images show immunofluorescence labeling of (A) p-ERK and (B) t-ERK in skin preparations subjected to different treatments. Eight independent experiments were performed. Scale bar=100 μm.
Figure 8:
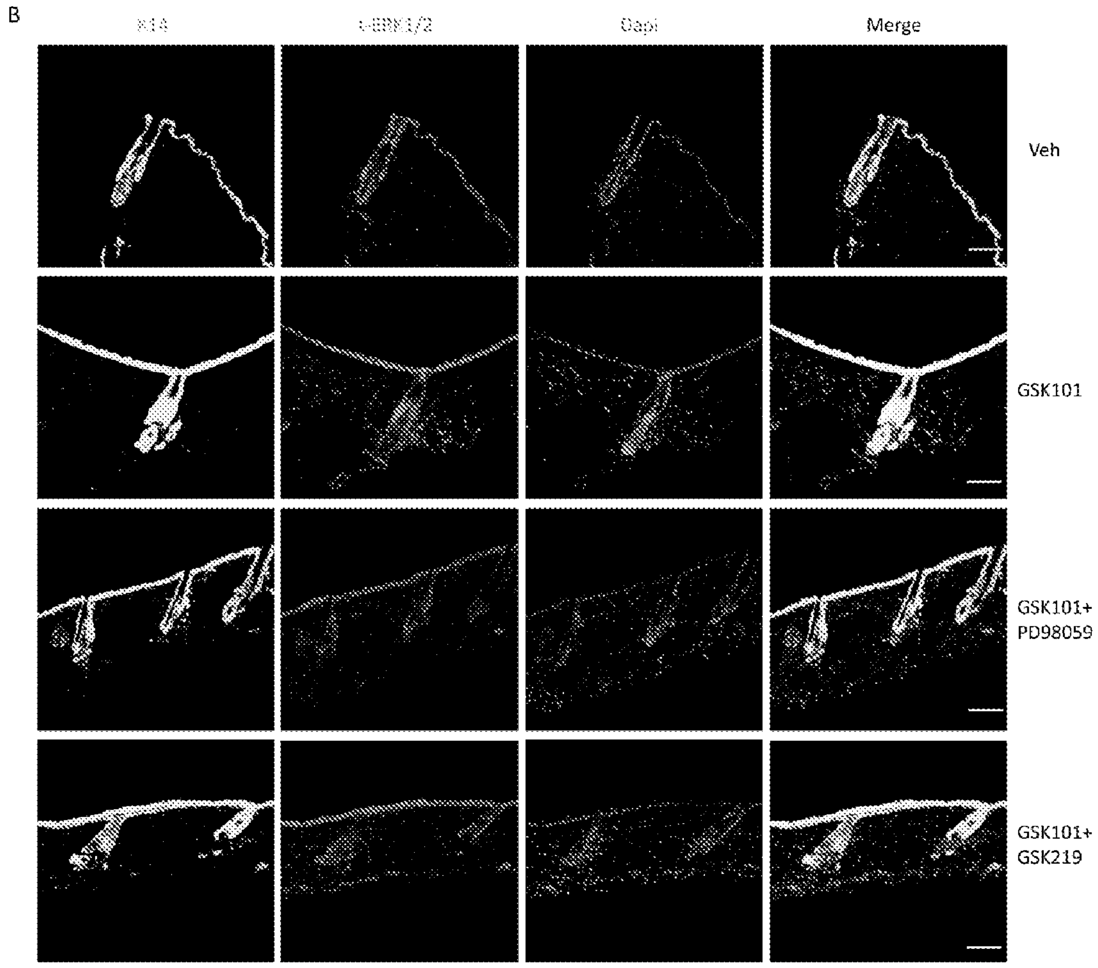

ERK Signaling is Critically Involved in TRPV4-Mediated Hair Follicle Regeneration Previous studies showed that TRPV4-mediated $Ca^{2+}$ influx activates downstream ERK signaling in mouse skin resulting in an acute scratching behavior to exogenously applied histamine (Chen et al., 2016). To investigate if ERK signaling is also involved in TRPV4-mediated hair follicle regeneration, PD98059, a selective inhibitor of MEK1 and the MAPK cascade, was used in mice subjected to a single intradermal injection of GSK1016790A. Strikingly, hair growth was completely absent from the PD98059-pretreated mice 17 days after GSK1016790A injection, while GSK1016790A persistently induced hair growth in vehicle-treated mice (FIG. 4*a*). In line with this finding, it was also found that ERK1/2 phosphorylation was significantly increased 15 min after a single intradermal injection of GSK1016790A, which was severely attenuated by pretreatment with either GSK2193874 or PD98059 (FIG. 4*b*, FIG. 4*c* and FIG. 8), further confirming that the activation of ERK signaling is required for TRPV4-mediated hair follicle regeneration.

To further determine whether ERK signaling is involved in TRPV4-mediated disruption of the balance of the inhibitory and activation factors that regulate hair follicle stem cell activity, GSK1016790A-induced changes in expression of Bmp6, Fgf18, Fgf7, Wnt16, and Nog was measured in the skin preparations of mice treated with PD98059 and vehicle control using real-time RT-PCR. Remarkably, PD98059 completely reversed the GSK1016790A-induced decrease in the expression of Bmp6 and Fgf18 and increase in the expression of Fgf7, Wnt16, and Nog (FIG. 4*d*), suggesting that ERK signaling downstream of TRPV4 activation is responsible for hair follicle regeneration by differentially regulating the expression of both inhibitory and activation factors that influence hair follicle stem cell telogen to anagen transition.

Figure 5:
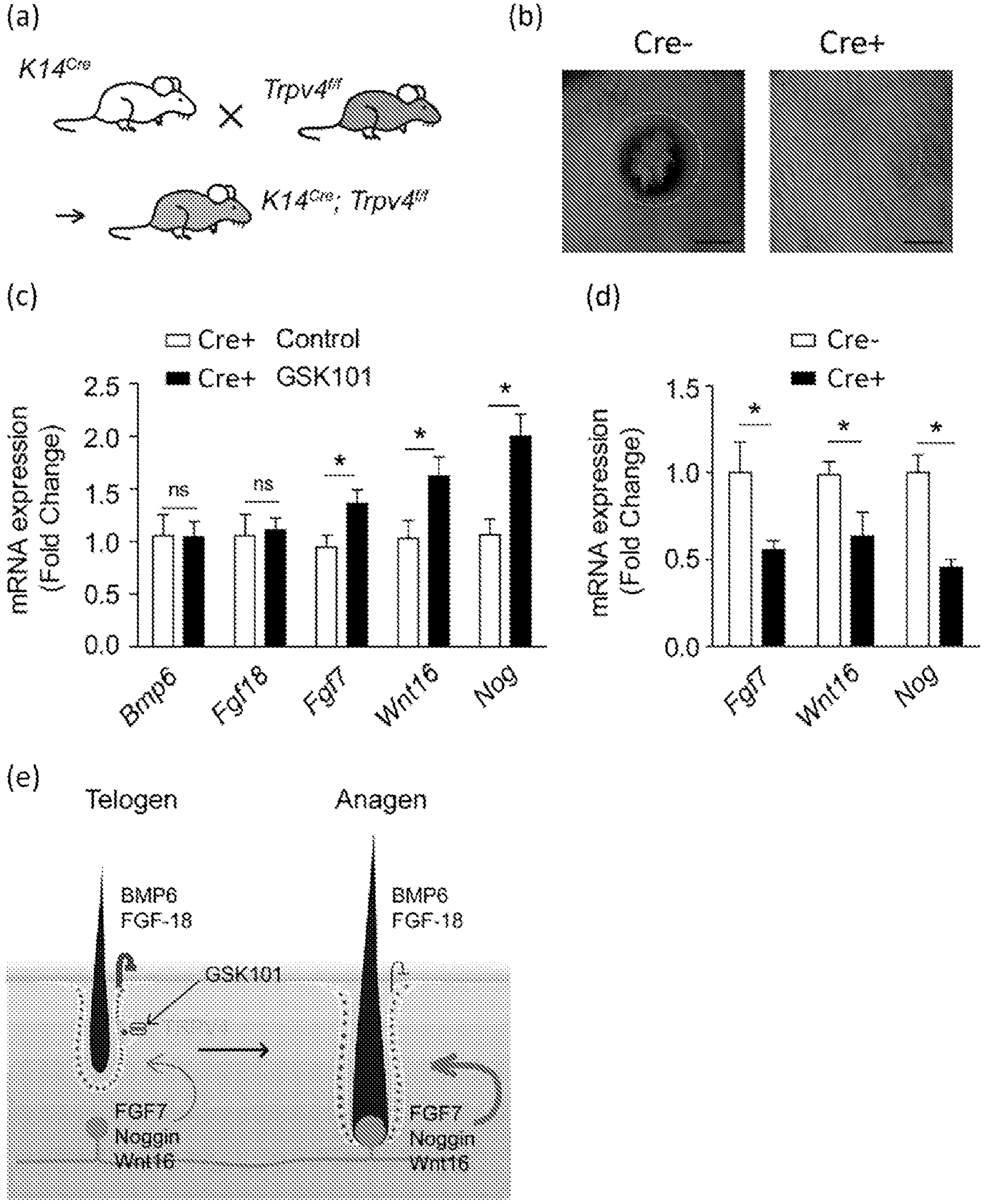
FIG. 5. Keratinocyte-specific ablation of TRPV4 function abolishes GSK1016790A (GSK101)-induced new hair growth as well as changes in Bmp6 and Fgf18 expression. (a) Schematic diagram showing the generation of $K14^{Cre}$. $Trpv4^{f/f}$ mice. (b) Representative images showing new hair growth in the $Cre^-$ but not the Cre+ $K14^{Cre}$; $Trpv4^{f/f}$ mice in response to intradermal GSK1016790A injections. Scale bar=0.5 cm. (c) Quantitative RT-PCR data obtained from whole skin lysates from the $Cre^+$ $K14^{Cre}$; $Trpv4^{f/f}$ mice show that GSK1016790A did not change the expression of Bmp6 and Fgf18 but increase the expression of Fgf7, Wnt16, and Nog. (d) Quantitative RT-PCR data showed that the increase of Fgf7, Wnt16, and Nog was significantly less in $Cre^+$ $K14^{Cre}$; $Trpv4^{f/f}$ than that in the wild-type mice. (e) Schematic diagram showing the telogen to anagen transition induced by GSK1016790A activation of TRPV4. Five independent experiments were performed. Data are mean±SEM. *P<0.05; n.s., non-significance.

TRPV4-Expressing Keratinocytes are Critically Involved in GSK1016790A-Induced Hair Follicle Regeneration Recent studies have demonstrated that skin-resident macrophages also contribute to hair follicle stem cell activation and hair follicle regeneration, especially when intensive macrophage infiltration occurs under inflammatory states induced by wound injury or topical application of imiquimod, an immune response modifier (Amberg, Holcmann, Stulnig, & Sibilia, 2016; Chen et al., 2015; Wang et al., 2017). Moreover, Ali et al. (2017) showed that the skin regulatory T (Treg) cells could enhance the activation and differentiation of epithelial stem cells, thereby promoting hair follicle cycling. Together, these findings highlight the importance of a crosstalk between the epithelial stem cell niche and micro-environment in hair follicle regeneration (Amberg et al., 2016; Wang et al., 2017). Since TRPV4 is also functionally expressed in dermal macrophages in addition to keratinocytes, both macrophage-specific and keratinocyte-specific TRPV4 conditional KO mice were engineered by crossing $Cx3cr1^{Cre}$ and $K14^{Cre}$ mice with $Trpv4^{f/f}$ mice, respectively, to determine whether TRPV4-expressing dermal macrophages and/or keratinocytes contribute to GSK1016790A-induced hair regeneration (FIG. 5*a*).

Figure 9:
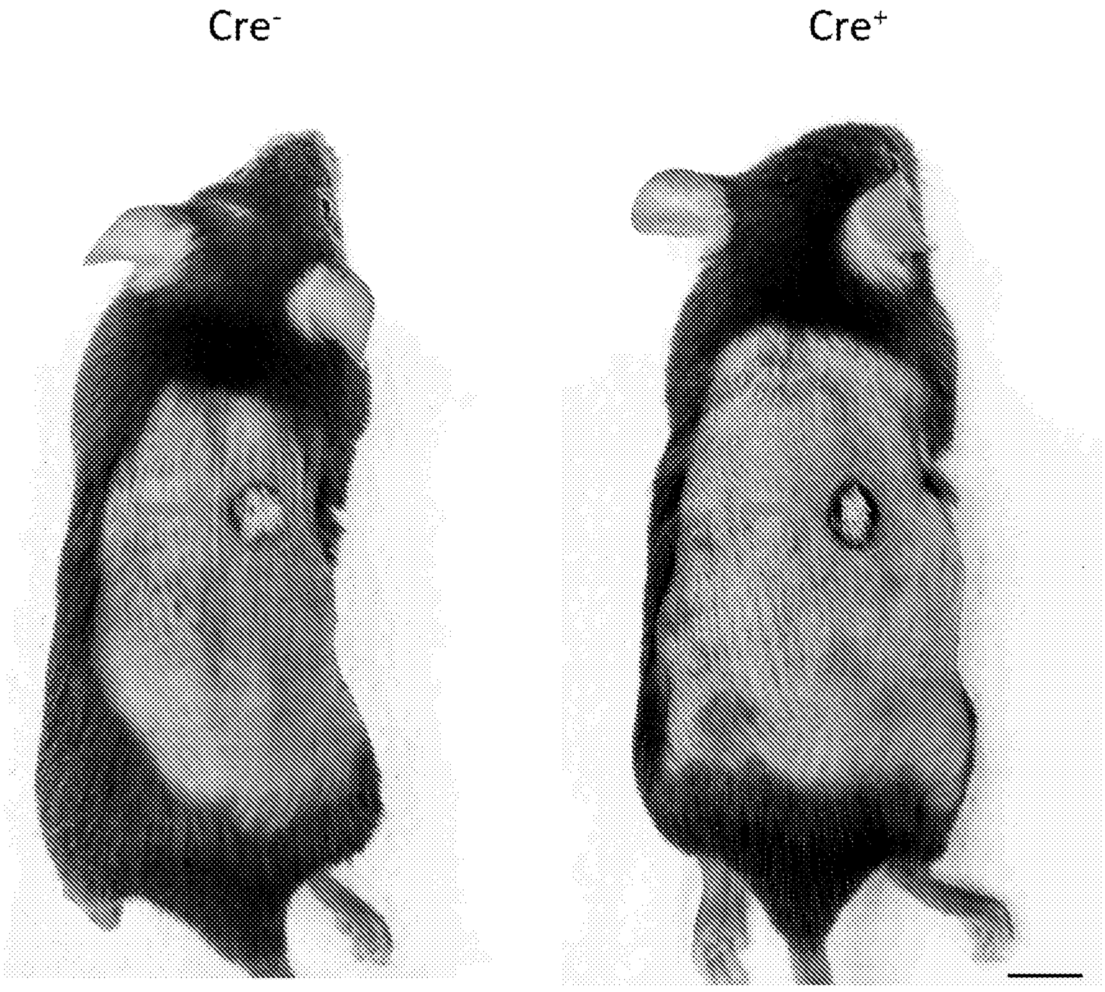
FIG. 9. Representative images showing comparable hair growth in both 7-week-old $Cre^+$ (n=5) and $Cre^-$ $Cx3cr1^{Cre}$; $Trpv4^{f/f}$ mice (n=5) after intradermal injections of GSK1016790A (GSK101). Scale bar=1 cm.

Interestingly, although TRPV4 is expressed by dermal macrophages, a single intradermal injection of GSK1016790A induced comparable hair regeneration in both $Cx3cr1^{Cre}$; $Trpv4^{f/f}$ mice and their $Cre^{-}$ wt littermates (FIG. 9). On the other hand, GSK1016790A-induced hair regeneration was completely absent from the $K14^{Cre}$; $Trpv4^{f/f}$ mice (FIG. 5*b*), recapitulating the hair growth phenotype seen in the global TRPV4 KO mice, while their $Cre^{-}$ wt littermates persistently had hair regeneration. Moreover, GSK1016790A treatment did not affect the mRNA expression levels of Bmp6 and Fgf18 in the $Cre^{+}$ $K14^{Cre}$; $Trpv4^{f/f}$ mice (FIG. 5*c*), further confirming keratinocytes origin of Bmp6 and Fgf18. Although the expression of Fgf7, Wnt16, and Nog was still increased after the GSK1016790A injection in the $Cre^{+}$ $K14^{Cre}$; $Trpv4^{f/f}$ mice (FIG. 5*c*), it was significantly decreased compared with that in wt mice injected with GSK1016790A (FIG. 5*d*). Taken together, these results suggest that acute chemical activation of TRPV4-expressing keratinocytes but not dermal macrophages is critical for breaking the quiescence of a hair follicle stem cell to initiate hair follicle telogen to anagen transition and induce hair regeneration.

Topical Application of GSK101 Increased Hair Growth

Figure 10:
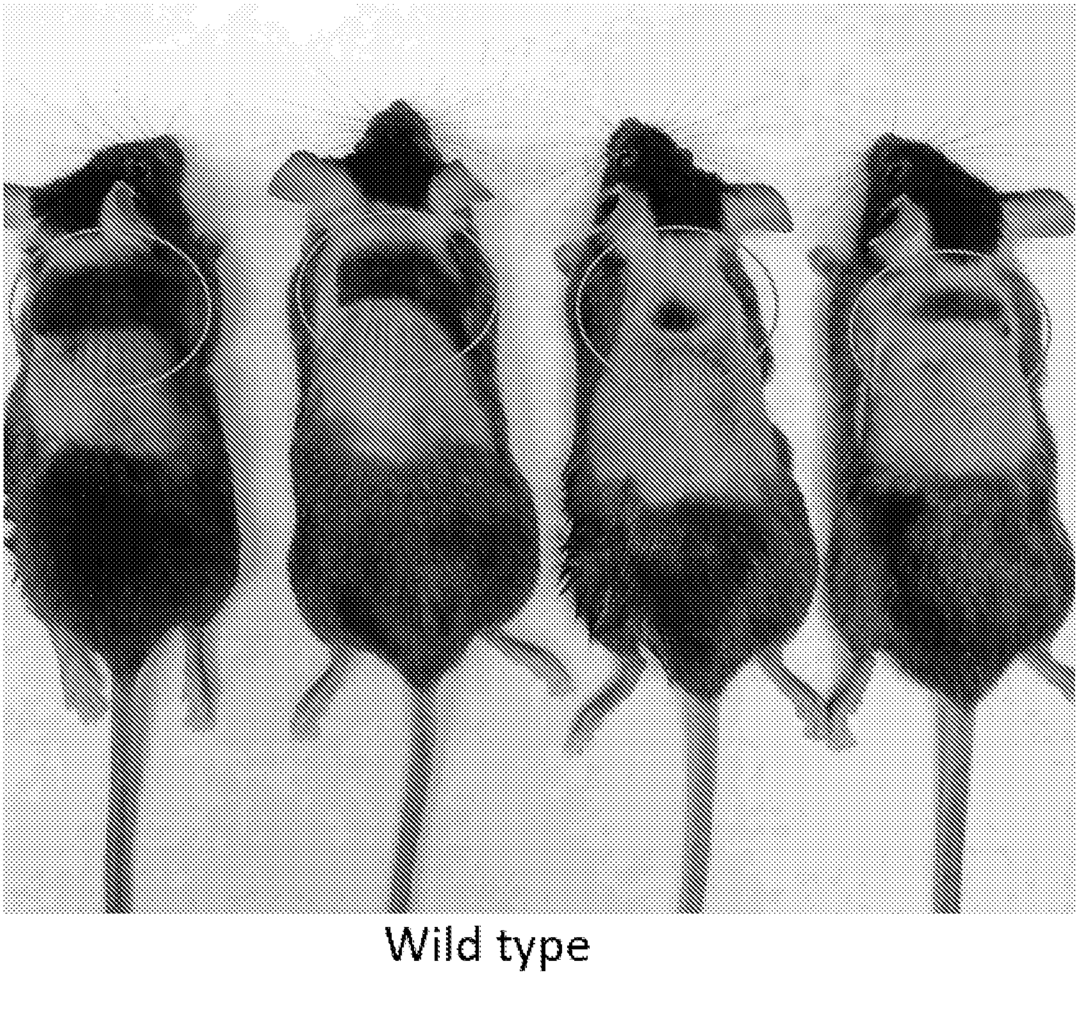
FIG. 10. Representative images on the left show that topically applied GSK101 at 100 μM at once increased hair growth when compared with topical application of vehicle in mice with tape striping of shaved back. Images were taken on day 12 after GSK101 treatment. Tape stripping only did not cause significant TRPV4-dependent hair growth (representative images below).
Figure 10:
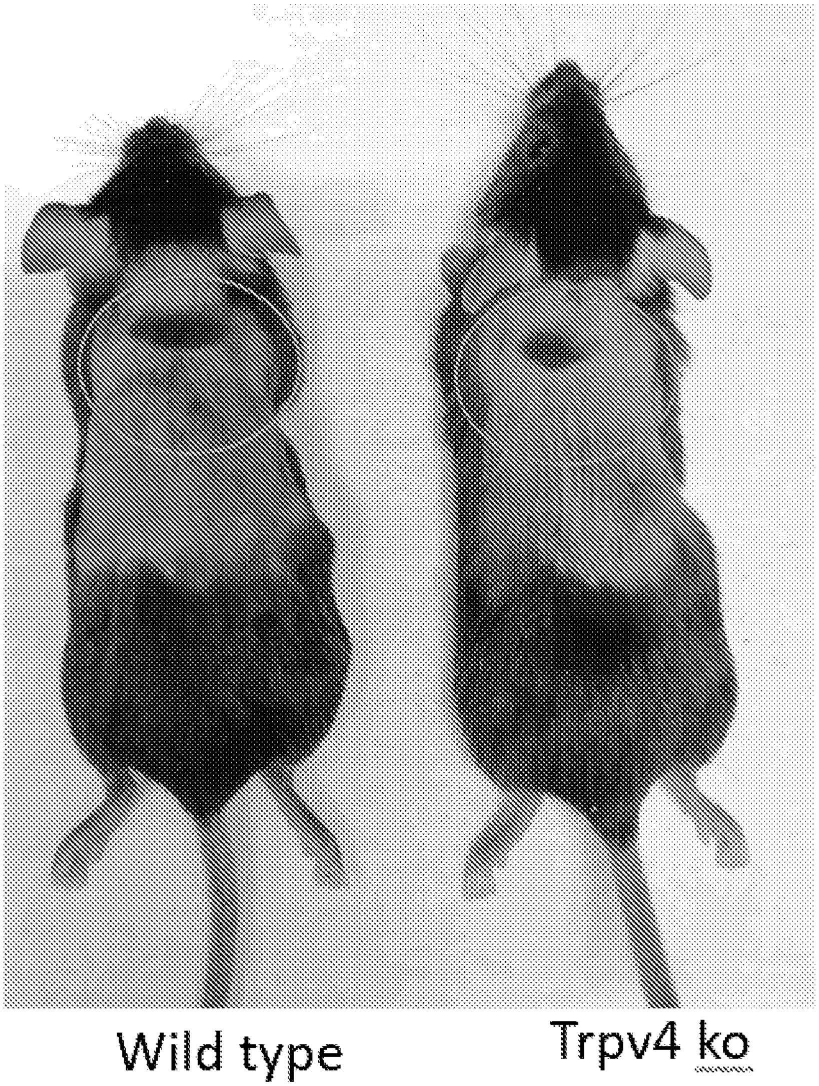

Shown here are topical applications of the TRPV4 activating agent or activator GSK101 on mice with tape stripping of back skin and found that could also facilitate hair growth compared with the vehicle. A TRPV4-dependent increase in hair growth was observed (FIG. 10).

Tape stripping was used to remove the stratum corneum to facilitate GSK101 entry into the skin. The agent can be applied with no additional agent or skin treatment method. The effect was removed by genetic ablation of the TRPV4 function.

DISCUSSION

In this study, it was demonstrated that transient activation of TRPV4 by a single intradermal injection of a small molecule agonist successfully induced telogen to anagen transition and hair follicle regeneration and growth of new hair in mice. This hair follicle regeneration occurred through TRPV4-mediated activation of ERK signaling that broke the hair follicle stem cell quiescence through both increasing the expression of chemical cues that promoted hair follicle stem cell activity and reducing the expression of chemical cues that suppressed hair follicle stem cell activity. Although recent studies showed that skin-resident macrophages can modulate keratinocyte proliferation and contribute to hair follicle regeneration induced by wound injury or imiquimod (Amberg et al., 2016; Wang et al., 2017), these results showed that the activation of TRPV4-expressing keratinocytes was required to induce hair follicle stem cell proliferation and regeneration. However, other types of TRPV4-expressing cells can also contribute to sustaining anagen entry by regulating the expression of Fgf7, Wnt16, and Nog. These findings have significantly advanced the understanding of the regulation of hair follicle stem cells by TRP channels and can help to develop effective hair follicle regenerative therapies.

Mouse skin hair follicle morphogenesis follows a precise timescale and there are two hair cycles in C57BL/6 mice during the first 14 weeks after birth (Muller-Rover et al., 2001; Paus & Cotsarelis, 1999). Many types of skin cells including stem cells in the bulge and dermal papilla, dermal fibroblasts, adipocytes, and dermal macrophages can produce a variety of chemical cues to regulate hair follicle stem cell activity (Greco et al., 2009; Hsu et al., 2011; Plikus et al., 2008). These results showed that TRPV4 activation by GSK1016790A caused a down-regulation of the expression of Fgf18 and Bmp6, both of which are anagen-inhibiting factors. On the other hand, the expression of promoting factors Fgf7, Wnt16, and Nog was significantly up-regulated following a single intradermal injection of GSK1016790A. Moreover, the decrease of Fgf18 may also initiate an up-regulation of Nog expression, whose gene product will further inhibit the expression of Bmp6 (Reinhold, Abe, Kapadia, Liao, & Naski, 2004; Song et al., 2010). These results suggested that transient chemical activation of TRPV4 shifted the balance of hair follicle stem cell inhibiting and promoting factors in early telogen, which initiated hair follicle regeneration. Additionally, it was shown that GSK1016790A had no effect on the expression of Bmp6 and Fgf18 in mice with epithelial cell-specific ablation of the TRPV4 function, which is consistent with a previous report that both Bmp6 and Fgf18 derive from skin keratinocytes (Hsu et al., 2011). Although the expression of three promoting factors was still increased after GSK1016790A injection in the keratinocyte-specific conditional TRPV4 KO mice, the increase was significantly reduced when compared with that in the $Cre^{-}$ wt littermates in response to GSK1016790A treatment. The increase of these genes in $K14^{Cre}$; $Trpv4^{f/f}$ mice indicated that other cell types expressing TRPV4 could also contribute to the increased expression of these genes, such as fibroblasts and adipocytes (Sharma et al., 2017; Ye et al., 2012). Therefore, although the absence of hair follicle regeneration in $K14^{Cre}$; $Trpv4^{f}$ f mice suggesting that K14-expressing keratinocytes play an essential role in GSK1016790A-induced hair follicle regeneration, it could not be excluded that there could be a possibility that neighboring fibroblasts, adipocytes, and dermal macrophages may also play some direct or indirect roles. Together, these results suggest that down-regulation of Bmp6 and Fgf18 likely is a prerequisite for TRPV4-mediated hair follicle regeneration and a combination of reducing the expression of the inhibiting factor and up-regulation of promoting factors of hair follicle function leads to hair follicle anagen initiation.

TRPV4 is a $Ca^{2+}$-permeable cation channel, the activation of which leads to increased intracellular $Ca^{2+}$ levels (Voets et al., 2002). Interestingly, $Ca^{2+}$-dependent ERK phosphorylation is required for VEGF-induced proliferation of dermal papilla cells (Li et al., 2012). Recent studies have also shown that ERK signaling pathway contributed to TRPV4-mediated acute chemical itch sensation and UVB-induced sunburn pain (Chen et al., 2016; Moore et al., 2013). Consistent with these findings, it was shown that GSK1016790A application induced a rapid ERK phosphorylation around the site of injection, which was blocked by the ERK inhibitor PD98059. More importantly, PD98059 pretreatment reversed both the changes in expression of hair follicle stem cell inhibiting and promoting factors as well as hair follicle regeneration induced by GSK1016790A, further supporting that ERK signaling was critical to TRPV4-mediated hair follicle regeneration.

Among TRP channels, TRPV3 and TRPV4 share many functional similarities in the skin: (1) both channels are expressed by skin keratinocytes and are activated by warm temperatures, (2) both channels are important for skin barrier function, and (3) like TRPV4, genetic ablation of TRPV3 function has no effect on general hair follicle cycling in mice (Cheng et al., 2010). TRPV3 was reported to play a differential role in hair follicle cycling. For instance, chemical activation of TRPV3 in cultured human hair follicles inhibited the hair shaft elongation and promoted the early catagen transformation (Borbiro et al., 2011). However, the gain-of-function mutation of TRPV3 inhibited the anagen to catagen transition, resulting in a prolonged anagen phase (Imura et al., 2007). One explanation for this discrepancy might be that the cellular toxicity produced by the constitutive channel activity of the gain-of-function TRPV3 mutation causes death of hair follicle keratinocytes as gain-of-function TRPV3 mutations induced marked cell death in vitro (Lin et al., 2012; Xiao, Tian, Tang, & Zhu, 2008). In marked contrast to a recent study showing that TRPV4 activation by GSK1016790A decreased the ratio of proliferating cells and increased the number of apoptotic cells in cultured human hair follicles ex vivo and presumably resulted in an inhibition of hair growth (Szabo et al., 2019), these results surprisingly showed that transient stimulation of the TRPV4-expressing hair follicle keratinocytes by a small molecule activator promoted hair follicle regeneration in vivo in mice. The discrepancy in these two studies might be caused by species differences in TRPV4 function in hair follicles between mice and humans as well as differences in experimental settings in which this study examined hair follicle regeneration in vivo, while Szabó et al. evaluated anagen maintenance ex vivo using cultured human hair follicles. Due to the species difference of mice and human skin where the anagen and telogen phases are interspersed, the dosage and timing of a small molecule activator for use in human skin may be different. Others have shown GSK101 activated membrane currents (PMID: 29293584) and induced IL-6 and IL-8 production in human epidermal keratinocytes HaCaT cells (PMID: 30022772). It would be also interesting to analyze the effect of TRPV4 activation in humans in vivo during a complete hair cycle, to determine whether anagen to catagen transition also occurs in humans.

In summary, it was demonstrated that transient chemical activation of TRPV4-expressing hair follicle keratinocytes shifts the balance of hair follicle stem cell inhibiting and promoting factors in telogen through ERK signaling, thereby promoting the telogen to anagen transition and hair follicle regeneration. This study advanced the understanding of the importance of TRPV4-expressing hair follicle keratinocytes in hair follicle regeneration, which might provide mechanistic insights into the development of effective therapeutic strategies for the treatment of hair loss and alopecia.

REFERENCES

Alexander, S. P. H., Roberts, R. E., Broughton, B. R. S., Sobey, S. G., George, C. H., Stanford, S. C., . . . Ahluwalia, A. (2018). Goals and practicalities of immunoblotting and immunohistochemistry: A guide for submission to the British Journal of Pharmacology. *British Journal of Pharmacology,* 175, 407-411. https://doi.org/10.1111/bph.14112

Alexander, S. P. H., Kelly, E., Mathie, A., Peters, J. A., Veale, E. L., Armstrong, J. F. (2019). The Concise Guide to PHARMACOLOGY 2019/20: Ion channels. *British Journal of Pharmacology,* 176, S142-S228.

Ali, N., Zirak, B., Rodriguez, R. S., Pauli, M. L., Truong, H. A., Lai, K., . . . Rosenblum, M. D. (2017). Regulatory T cells in skin facilitate epithelial stem cell differentiation. *Cell,* 169(1119-1129), ell11.

Amberg, N., Holcmann, M., Stulnig, G., & Sibilia, M. (2016). Effects of imiquimod on hair follicle stem cells and hair cycle progression. *The Journal of Investigative Dermatology,* 136, 2140-2149. https://doi.org/10.1016/j.jid.2016.06.613

Borbiro, I., Lisztes, E., Toth, B. I., Czifra, G., Olah, A., Szollosi, A. G., Biró, T. 2011). Activation of transient receptor potential vanilloid-3 inhibits human hair growth. *The Journal of Investigative Dermatology,* 131, 1605-1614. https://doi.org/10.1038/jid.2011.122

Caterina, M. J., & Pang, Z. (2016). TRP channels in skin biology and pathophysiology. *Pharmaceuticals* (Basel), 9. https://doi.org/10.3390/ph9040077

Chen, C. C., Wang, L., Plikus, M. V., Jiang, T. X., Murray, P. J., Ramos, R., . . . Chuong, C. M. (2015). Organ-level quorum sensing directs regeneration in hair stem cell populations. *Cell,* 161, 277-290. https://doi.org/10.1016/j.cell.2015.02.016

Chen, Y., Fang, Q., Wang, Z., Zhang, J. Y., MacLeod, A. S., Hall, R. P. Iiedtke, W. B., (2016). Transient receptor potential vanilloid 4 ion channel functions as a pruriceptor in epidermal keratinocytes to evoke histaminergic itch. *The Journal of Biological Chemistry,* 291, 10252-10262. https://doi.org/10.1074/jbc.M116.716464

Cheng, X., Jin, J., Hu, L., Shen, D., Dong, X. P., Samie, M. A., . . . Xu, H. (2010). TRP channel regulates EGFR signaling in hair morphogenesis and skin barrier formation. *Cell,* 141, 331-343. https://doi.org/10.1016/j.cell.2010.03.013

Curtis, M. J., Alexander, S., Cirino, G., Docherty, J. R., George, G. H., Giembycz, M. A., . . . Ahluwali, A. (2018). Experimental design and analysis and their reporting II: updated and simplified guidance for authors and peer reviewers. *British Journal of Pharmacology,* 175, 987-993. https://doi.org/10.1111/bph.14153

Denda, M., Sokabe, T., Fukumi-Tominaga, T., & Tominaga, M. (2007). Effects of skin surface temperature on epidermal permeability barrier homeostasis. *The Journal of Investigative Dermatology,* 127, 654-659. https://doi.org/10.1038/sj.jid.5700590

Enshell-Seijffers, D., Lindon, C., Kashiwagi, M., & Morgan, B. A. (2010). β-catenin activity in the dermal papilla regulates morphogenesis and regeneration of hair. *Developmental Cell,* 18, 633-642. https://doi.org/10.1016/j.devcel.2010.01.016

Gazzerro, E., Gangji, V., & Canalis, E. (1998). Bone morphogenetic proteins induce the expression of noggin, which limits their activity in cultured rat osteoblasts. *The Journal of Clinical Investigation,* 102, 2106-2114. https://doi.org/10.1172/JC13459

Greco, V., Chen, T., Rendl, M., Schober, M., Pasolli, H. A., Stokes, N., . . . Fuchs, E. (2009). A two-step mechanism for stem cell activation during hair regeneration. *Cell Stem Cell,* 4, 155-169. https://doi.org/10.1016/j.stem.2008.12.009

Harding, S. D., Sharman, J. L., Faccenda, E., Southan, C., Pawson, A. J., Ireland, S., . . . NC-IUPHAR. (2018). The IUPHAR/BPS Guide to PHARMACOLOGY in 2018: Updates and expansion to encompass the new guide to IMMUNOPHARMACOLOGY. *Nucleic Acids Research,* 46, D1091-D1106. https://doi.org/10.1093/nar/gkxl121

Hsu, Y. C., Pasolli, H. A., & Fuchs, E. (2011). Dynamics between stem cells, niche, and progeny in the hair follicle. *Cell,* 144, 92-105. https://doi.org/10.1016/j.cell.2010.11.049

Imura, K., Yoshioka, T., Hikita, I., Tsukahara, K., Hirasawa, T., Higashino, K., . . . Sakata, T. (2007). Influence of TRPV3 mutation on hair growth cycle in mice. *Biochemical and Biophysical Research Communications,* 363, 479-483. https://doi.org/10.1016/j.bbrc.2007.08.170

Ito, H., Akiyama, H., Shigeno, C., & Nakamura, T. (1999). Noggin and bone morphogenetic protein-4 coordinately regulate the progression of chondrogenic differentiation in mouse clonal EC cells, ATDC5. *Biochemical and Biophysical Research Communications,* 260, 240-244. https://doi.org/l0.1006/bbrc.l1999.0882

Kandyba, E., Leung, Y., Chen, Y. B., Widelitz, R., Chuong, C. M., & Kobielak, K. (2013). Competitive balance of intrabulge BMP/Wnt signaling reveals a robust gene network ruling stem cell homeostasis and cyclic activation. *Proceedings of the National Academy of Sciences of the United States of America,* 110, 1351-1356. https://doi.org/10.1073/pnas.1121312110

Kida, N., Sokabe, T., Kashio, M., Haruna, K., Mizuno, Y., Suga, Y., . . . Tominaga, M. (2012). Importance of transient receptor potential vanilloid 4 (TRPV4) in epidermal barrier function in human skin keratinocytes. *Pflügers Archiv,* 463, 715-725. https://doi.org/10.1007/s00424-012-1081-3

Kilkenny, C., Browne, W., Cuthill, I. C., Emerson, M., & Altman, D. G. (2010). Animal research: Reporting in vivo experiments: The ARRIVE guidelines. *British Journal of Pharmacology,* 160, 1577-1579.

Li, W., Man, X. Y., Li, C. M., Chen, J. Q., Zhou, J., Cai, S. Q., . . . Zheng, M. (2012). VEGF induces proliferation of human hair follicle dermal papilla cells through VEGFR-2-mediated activation of ERK. *Experimental Cell Research,* 318, 1633-1640. https://doi.org/10.1016/j.yexcr.2012.05.003

Lin, Z., Chen, Q., Lee, M., Cao, X., Zhang, J., Ma, D., . . . Yang, Y. (2012). Exome sequencing reveals mutations in TRPV3 as a cause of Olmsted syndrome. *American Journal of Human Genetics,* 90, 558-564. https://doi.org/10.1016/j.ajhg.2012.02.006

Luo, J., Feng, J., Yu, G., Yang, P., Mack, M. R., Du, J., Hu, H. (2018). Transient receptor potential vanilloid 4-expressing macrophages and keratinocytes contribute differentially to allergic and nonallergic chronic itch. *The Journal of Allergy and Clinical Immunology,* 141(608-619), e7.

Luo, J., & Hu, H. (2014). Thermally activated TRPV3 channels. *Current Topics in Membranes,* 74, 325-364. https://doi.org/10.1016/B978-0-12-800181-3.00012-9

Mamenko, M., Zaika, O., Boukelmoune, N., O'Neil, R. G., & Pochynyuk, O. (2015). Deciphering physiological role of the mechanosensitive TRPV4 channel in the distal nephron. *American Journal of Physiology. Renal Physiology,* 308, F275-F286. https://doi.org/10.1152/ajprenal.00485.2014

McGrath, J. C., & Lilley, E. (2015). Implementing guidelines on reporting research using animals (ARRIVE etc.): New requirements for publication in BJP. *British Journal of Pharmacology,* 172, 3189-3193. https://doi.org/10.1111/bph.12955

Moore, C., Cevikbas, F., Pasolli, H. A., Chen, Y., Kong, W., Kempkes, C., . . . Liedtke, W. B. (2013). UVB radiation generates sunburn pain and affects skin by activating epidermal TRPV4 ion channels and triggering endothelin-1 signaling. *Proceedings of the National Academy of Sciences of the United States of America,* 110, E3225-E3234. https://doi.org/10.1073/pnas.1312933110

Muller-Rover, S., Foitzik, K., Handjiski, B, Van der Veen, S., Eichmuller, K. S., Stenn, (2001). A comprehensive guide for the accurate classification of murine hair follicles in distinct hair cycle stages. *The Journal of Investigative Dermatology,* 117, 3-15. https://doi.org/10.1046/j.0022-202x.2001.01377.x Nilius, B., & Szallasi, A. (2014). Transient receptor potential channels as drug targets: From the science of basic research to the art of medicine. *Pharmacological Reviews,* 66, 676-814. https://doi.org/10.1124/pr.113.008268

Oshima, H., Rochat, A., Kedzia, C., Kobayashi, K., & Barrandon, Y. (2001). Morphogenesis and renewal of hair follicles from adult multipotent stem cells. *Cell,* 104, 233-245. https://doi.org/10.1016/S0092-8674(01)00208-2

Paus, R., & Cotsarelis, G. (1999). The biology of hair follicles. *The New England Journal of Medicine,* 341, 491-497. https://doi.org/10.1056/NEJM199908123410706

Plikus, M. V., Mayer, J. A., de la Cruz, D., Baker, R. E., Maini, P. K., Maxson, R., & Chuong, C. M. (2008). Cyclic dermal BMP signaling regulates stem cell activation during hair regeneration. *Nature,* 451, 340-344. https://doi.org/i0.1038/nature06457

Reinhold, M. I., Abe, M., Kapadia, R. M., Liao, Z., & Naski, M. C. (2004). FGF18 represses noggin expression and is induced by calcineurin. *The Journal of Biological Chemistry,* 279, 38209-38219. https://doi.org/10.1074/jbc.M404855200

Schmidt-Ullrich, R., & Paus, R. (2005). Molecular principles of hair follicle induction and morphogenesis. *BioEssays,* 27, 247-261. https://doi.org/10.1002/bies.20184

Sharma, S., Goswami, R., Merth, M., Cohen, J., Lei, K. Y., Zhang, D. X., & Rahaman, S. O. (2017). TRPV4 ion channel is a novel regulator of dermal myofibroblast differentiation. *American Journal of Physiology. Cell Physiology,* 312, C562-C572. https://doi.org/10.1152/ajpcell.00187.2016

Sokabe, T., Fukumi-Tominaga, T., Yonemura, S., Mizuno, A., & Tominaga, M. (2010). The TRPV4 channel contributes to intercellular junction formation in keratinocytes. *The Journal of Biological Chemistry,* 285, 18749-18758. https://doi.org/10.1074/jbc.M110.103606

Sokabe, T., & Tominaga, M. (2010). The TRPV4 cation channel: A molecule linking skin temperature and barrier function. *Communicative & Integrative Biology,* 3, 619-621. https://doi.org/10.4161/cib.3.6.13461

Song, K., Krause, C., Shi, S., Patterson, M., Suto, R., Grgurevic, L., . . . Alaoui-Ismaili, M. H. (2010). Identification of a key residue mediating bone morphogenetic protein (BMP)-6 resistance to noggin inhibition allows for engineered BMPs with superior agonist activity. *The Journal of Biological Chemistry,* 285, 12169-12180. https://doi.org/10.1074/jbc.M109.087197

Suzuki, M., Mizuno, A., Kodaira, K., & Imai, M. (2003). Impaired pressure sensation in mice lacking TRPV4. *The Journal of Biological Chemistry,* 278(25), 22664-22668. https://doi.org/10.1074/jbc.M302561200

Szabo, I. L., Herczeg-Lisztes, E., Szegedi, A., Nemes, B., Paus, R., Biro, T., Szöllöi, . . . (2019). TRPV4 is expressed in human hair follicles and inhibits hair growth in vitro. *The Journal of Investigative Dermatology,* 139, 1385-1388. https://doi.org/10.1016/j.jid.2018.11.020

Thorneloe, K. S., Cheung, M., Bao, W., Alsaid, H., Lenhard, S., Jian, M. Y., Willette, R. N. (2012). An orally active TRPV4 channel blocker prevents and resolves pulmonary edema induced by heart failure. *Science Translational Medicine,* 4, 159ra148.

Thorneloe, K. S., Sulpizio, A. C., Lin, Z., Figueroa, D. J., Clouse, A. K., McCafferty, G. P., . . . Westfall, T. D. (2008). N-((1S)-1-{[4-((2S)-2-{[(2,4-dichlorophenyl) sulfonyl]amino}-3-hydroxypropanoyl)-1-piperazinyl] carbonyl}-3-methylbutyl)-1-benzothiophene-2-carboxamide (GSK1016790A), a novel and potent transient receptor potential vanilloid 4 channel agonist induces urinary bladder contraction and hyperactivity: Part I. *The Journal of Pharmacology and Experimental Therapeutics,* 326, 432-442. https://doi.org/10.1124/jpet.108.139295

Toth, B. I., Olah, A., Szollosi, A. G., & Biro, T. (2014). TRP channels in the skin. *British Journal of Pharmacology,* 171, 2568-2581. https://doi.org/10.1111/bph.12569

Voets, T. (2014). TRP channels and thermosensation. *Handbook of Experimental Pharmacology,* 223, 729-741. https://doi.org/i0.1007/978-3-319-05161-1_1

Voets, T., Prenen, J., Vriens, J., Watanabe, H., Janssens, A., Wissenbach, U., . . . Nilius, B. (2002). Molecular determinants of permeation through the cation channel TRPV4. *Journal of Biological Chemistry,* 277, 33704-33710. https://doi.org/10.1074/jbc.M204828200

Wang, X., Chen, H., Tian, R., Zhang, Y., Drutskaya, M. S., Wang, C., . . . Wu, Y. (2017). Macrophages induce AKT/β-catenin-dependent $Lgr5^+$ stem cell activation and hair follicle regeneration through TNF. *Nature Communications,* 8, 14091. https://doi.org/10.1038/ncomms14091

Xiao, R., Tian, J., Tang, J., & Zhu, M. X. (2008). The TRPV3 mutation associated with the hairless phenotype in rodents is constitutively active. *Cell Calcium,* 43, 334-343. https://doi.org/10.1016/j.ceca.2007.06.004

Ye, L., Kleiner, S., Wu, J., Sah, R., Gupta, R. K., Banks, A. S., . . . Spiegelman, B. M. (2012). TRPV4 is a regulator of adipose oxidative metabolism, inflammation, and energy homeostasis. *Cell,* 151, 96-110. https://doi.org/10.1016/j.cell.2012.08.034

What is claimed is:

1. A method of treating hair loss or promoting hair growth comprising administering a therapeutically effective amount of a TRPV4 activating agent to a subject in need thereof, wherein the TRPV4 activating agent is selected from the group consisting of: RN 1747; 5,6-EET: Bisandrographolide A; Dimethylallyl pyrophosphate; and combinations thereof.

2. A method of inducing hair follicle regeneration comprising administering a TRPV4 activating agent to a subject in need thereof, wherein the TRPV4 activating agent is selected from the group consisting of: RN 1747; 5,6-EET; Bisandrographolide A; Dimethylallyl pyrophosphate; and combinations thereof.

3. A method of inducing telogen-anagen transition in a hair follicle cell comprising administering a therapeutically effective amount of a TRPV4 activating agent to a subject in need thereof, wherein the TRPV4 activating agent is selected from the group consisting of: RN 1747; 5,6-EET; Bisandrographolide A: Dimethylallyl pyrophosphate; and combinations thereof.

4. The method of claim 3, wherein the hair follicle cell is selected from a quiescent stem cell or TRPV4-expressing cell.

5. The method of claim 4, wherein the TRPV4-expressing cell is a fibroblast or adipocyte.

6. A method of increasing expression or upregulating an anagen-activating factor and decreasing expression of or downregulating an anagen-inhibiting factor in a cell comprising administering a TRPV4 activating agent to the cell, wherein the TRPV4 activating agent is selected from the group consisting of: RN 1747; 5,6-EET; Bisandrographolide A; Dimethylallyl pyrophosphate; and combinations thereof.

7. The method of claim 1, wherein the subject has alopecia.

8. The method of claim 1, wherein the subject has thinning hair.

9. The method of claim 1, wherein the subject has telogen effluvium.

10. The method of claim 1, wherein the subject has male pattern baldness.

11. The method of claim 1, wherein the subject has hair loss or hair thinning associated with cellular quiescence or dormancy of hair follicles.

12. The method of claim 1, wherein the TRPV4 activating agent is administered intradermally or topically.

13. The method of claim 1, wherein the TRPV4 activating agent is administered via microneedle injection, intraperitoneally, intradermally, topically, or orally.

14. The method of claim 1, wherein the TRPV4 activating agent is administered intradermally by microneedle injection.

15. The method of claim 1, wherein the therapeutically effective amount of the TRPV4 activating agent is an amount sufficient to induce telogen to anagen transition and hair follicle regeneration compared to a control or compared to the subject prior to being administered the TRPV4 activating agent.

16. The method of claim 1, wherein the therapeutically effective amount of the TRPV4 activating agent is an amount sufficient to increase proliferation of hair follicle keratinocytes compared to a control or compared to the subject prior to being administered the TRPV4 activating agent.

17. The method of claim 1, wherein the therapeutically effective amount of the TRPV4 activating agent is an amount sufficient to increase an amount of Ki67-positive K14-expressing hair follicle keratinocytes or stem cells compared to a control or compared to the subject prior to being administered the TRPV4 activating agent.

18. The method of claim 1, wherein the therapeutically effective amount of the TRPV4 activating agent is an amount effective to:

increase or upregulate expression of one or more anagen-promoting factors and decrease or downregulate expression of one or more anagen-inhibiting factors compared to a control or compared to the subject prior to being administered the TRPV4 activating agent.

19. The method of claim 18, wherein the one or more anagen-promoting factors are selected from Fgf7, Wnt16, or Nog; and the one or more anagen-inhibiting factors are selected from Fgf18 or Bmp6.

20. The method of claim 1, wherein the therapeutically effective amount of the TRPV4 activating agent is an amount sufficient to increase ERK1/2 phosphorylation compared to a control or compared to the subject prior to being administered the TRPV4 activating agent.

21. The method of claim 1, wherein the TRPV4 activating agent is administered in one treatment or multiple treatments over a time course of treatment.

22. The method of claim 1, wherein the TRPV4 activating agent comprises dCas9 fused or interacts with a transcriptional activator, leading to activation of genetic expression of TRPV4, TRPV4 function, or TRPV4 activity.

* * * * *

SEQUENCE LISTING

<160> NUMBER OF SEQ ID NOS: 12

<210> SEQ ID NO 1
<211> LENGTH: 26
<212> TYPE: DNA
<213> ORGANISM: Artificial Sequence
<220> FEATURE:
<223> OTHER INFORMATION: Synthetic Primer

<400> SEQUENCE: 1
agcacagaga ctctgaccta tttttg 26

<210> SEQ ID NO 2
<211> LENGTH: 23
<212> TYPE: DNA
<213> ORGANISM: Artificial Sequence
<220> FEATURE:
<223> OTHER INFORMATION: Synthetic primer

<400> SEQUENCE: 2
ccacagattg ctagttgctg tga 23

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
ttgtggcaat caaaggggtg 20

<210> SEQ ID NO 4
<211> LENGTH: 23
<212> TYPE: DNA
<213> ORGANISM: Artificial Sequence
<220> FEATURE:
<223> OTHER INFORMATION: Synthetic primer

<400> SEQUENCE: 4
cctccgctgt gtgtccattt agc 23

<210> SEQ ID NO 5
<211> LENGTH: 26
<212> TYPE: DNA
<213> ORGANISM: Artificial Sequence
<220> FEATURE:
<223> OTHER INFORMATION: Synthetic primer

<400> SEQUENCE: 5
gaattctacc tgtgtatgaa ccgaaa 26

<210> SEQ ID NO 6
<211> LENGTH: 22
<212> TYPE: DNA
<213> ORGANISM: Artificial Sequence
<220> FEATURE:
<223> OTHER INFORMATION: Synthetic primer

<400> SEQUENCE: 6
tgaacacgca ctccttgcta gt 22

<210> SEQ ID NO 7
<211> LENGTH: 20
<212> TYPE: DNA
<213> ORGANISM: Artificial Sequence -continued

```
<220> FEATURE:
<223> OTHER INFORMATION: Synthetic primer

<400> SEQUENCE: 7

agagtgcaac cggacatcag                                                20


<210> SEQ ID NO 8
<211> LENGTH: 22
<212> TYPE: DNA
<213> ORGANISM: Artificial Sequence
<220> FEATURE:
<223> OTHER INFORMATION: Synthetic primer

<400> SEQUENCE: 8

cgtagcagca ccagataaac tt                                             22


<210> SEQ ID NO 9
<211> LENGTH: 19
<212> TYPE: DNA
<213> ORGANISM: Artificial Sequence
<220> FEATURE:
<223> OTHER INFORMATION: Synthetic primer

<400> SEQUENCE: 9

cctggtggac ctcatcgaa                                                 19


<210> SEQ ID NO 10
<211> LENGTH: 21
<212> TYPE: DNA
<213> ORGANISM: Artificial Sequence
<220> FEATURE:
<223> OTHER INFORMATION: Synthetic primer

<400> SEQUENCE: 10

cagcgtctcg ttcagatcct t                                              21


<210> SEQ ID NO 11
<211> LENGTH: 21
<212> TYPE: DNA
<213> ORGANISM: Artificial Sequence
<220> FEATURE:
<223> OTHER INFORMATION: Synthetic primer

<400> SEQUENCE: 11

aggtcggtgt gaacggattt g                                              21


<210> SEQ ID NO 12
<211> LENGTH: 23
<212> TYPE: DNA
<213> ORGANISM: Artificial Sequence
<220> FEATURE:
<223> OTHER INFORMATION: Synthetic primer

<400> SEQUENCE: 12

tgtagaccat gtagttgagg tca                                            23
```